(12) United States Patent
Shifflett et al.

(10) Patent No.: US 11,927,552 B2
(45) Date of Patent: Mar. 12, 2024

(54) SYSTEMS AND METHODS FOR COSMOGENIC NEUTRON SENSING MOISTURE DETECTION IN AGRICULTURAL SETTINGS

(71) Applicant: QUAESTA INSTRUMENTS, LLC, Tucson, AZ (US)

(72) Inventors: Peter Shifflett, Tucson, AZ (US); Gary Womack, Tucson, AZ (US); Steven Hamann, Tucson, AZ (US)

(73) Assignee: QUAESTA INSTRUMENTS, LLC, Tucson, AZ (US)

(*) Notice: Subject to any disclaimer, the term of this patent is extended or adjusted under 35 U.S.C. 154(b) by 86 days.

(21) Appl. No.: 17/499,614

(22) Filed: Oct. 12, 2021

(65) Prior Publication Data
US 2022/0113267 A1    Apr. 14, 2022

Related U.S. Application Data

(60) Provisional application No. 63/090,596, filed on Oct. 12, 2020.

(51) Int. Cl.
*G01N 23/204*    (2006.01)
*G01N 23/20008*    (2018.01)
(Continued)

(52) U.S. Cl.
CPC ..... *G01N 23/204* (2013.01); *G01N 23/20008* (2013.01); *G01N 33/246* (2013.01);
(Continued)

(58) Field of Classification Search
CPC .... G01N 23/203; G01N 23/204; G01N 23/22; G01N 23/221; G01N 23/222;
(Continued)

(56) References Cited

U.S. PATENT DOCUMENTS

| 2,928,965 A | 10/1954 | Bayard et al. |
| 4,047,042 A | 9/1977 | Wada et al. ................... 250/390 |

(Continued)

OTHER PUBLICATIONS

Andreasen et al., "Cosmic-ray neutron transport at a forest field site: the sensitivity to various environmental conditions with focus on biomass and canopy interception", Hydrology and Earth System Sciences, vol. 21, No. 4, Apr. 3, 2017, 20 pgs.

(Continued)

*Primary Examiner* — Allen C. Ho
(74) *Attorney, Agent, or Firm* — HAYES SOLOWAY P.C.

(57) ABSTRACT

An apparatus for cosmogenic neutron sensing to detect moisture includes a thermal neutron proportional counter. A housing is formed at least partially from a moderating material, which is positioned around the thermal neutron proportional counter. A proportional counter electronics unit is within the housing and has a preamplifier and a shaping amplifier. The preamplifier and shaping amplifier are directly connected to the thermal neutron proportional counter. At least one photovoltaic panel provides electrical power to the thermal neutron proportional counter. A data logger is positioned vertically above the thermal neutron proportional counter and proportional counter electronics unit. A signal from the thermal neutron proportional counter is transmitted through the proportional counter electronics unit and is received by the data logger. The signal indicates a moisture content within a measurement surface of the thermal neutron proportional counter.

20 Claims, 16 Drawing Sheets

(51) Int. Cl.
  *G01N 33/24* (2006.01)
  *G01V 5/00* (2006.01)
  *H02S 20/32* (2014.01)
  *H01Q 1/24* (2006.01)

(52) U.S. Cl.
  CPC ............ *G01V 5/0075* (2013.01); *H02S 20/32* (2014.12); *G01N 2033/245* (2013.01); *G01N 2223/05* (2013.01); *G01N 2223/053* (2013.01); *G01N 2223/063* (2013.01); *G01N 2223/1063* (2013.01); *G01N 2223/1066* (2013.01); *G01N 2223/205* (2013.01); *G01N 2223/301* (2013.01); *G01N 2223/613* (2013.01); *H01Q 1/24* (2013.01)

(58) Field of Classification Search
  CPC ....... G01N 2223/053; G01N 2223/063; G01N 2223/074; G01N 2223/0745; G01N 2223/106; G01N 2223/1063; G01N 2223/1066; G01N 2223/205; G01N 2223/301; G01N 2223/613; G01N 2223/054; G01V 5/0025; G01V 5/0066; G01V 5/0069; G01V 5/0075; G01V 5/0091; G01V 5/10; G01V 5/104; G01V 5/105; G01V 5/107; G01V 5/108
  USPC ......... 250/253, 269.4, 269.5, 370.05, 390.01
  See application file for complete search history.

(56) References Cited

U.S. PATENT DOCUMENTS

| | | | | |
|---|---|---|---|---|
| 4,463,264 | A | 7/1984 | Young et al. ................. | 250/390 |
| 4,645,935 | A * | 2/1987 | Salaita ................... | G01N 23/09 250/391 |
| 4,992,667 | A | 2/1991 | Abelentsev et al. ...... | 250/390.05 |
| 5,083,029 | A | 1/1992 | Buchanan ................. | 250/390.05 |
| 5,258,622 | A * | 11/1993 | Pratt, Jr. .............. | G01N 33/383 250/390.05 |
| 5,321,269 | A | 6/1994 | Kitaguchi et al. ........ | G01T 3/08 |
| 5,502,303 | A | 3/1996 | Gonzalez-Lepera ....... | 250/252.1 |
| 7,078,705 | B1 | 7/2006 | Ianakiev et al. ......... | 250/390.01 |
| 7,233,007 | B2 | 6/2007 | Downing et al. ........ | 250/390.11 |
| 7,514,694 | B2 | 4/2009 | Stephan et al. ......... | 250/390.01 |
| 7,902,513 | B2 * | 3/2011 | Kub ......................... | G01T 3/08 250/370.05 |
| 8,217,360 | B2 | 7/2012 | Nukatsuka et al. ...... | 250/370.11 |
| 8,653,470 | B2 | 2/2014 | Dubeau .................... | 250/390.07 |
| 8,796,634 | B2 | 8/2014 | Kisner et al. ........... | G01T 3/008 |
| 9,029,788 | B2 | 5/2015 | Yang et al. ............... | G01T 3/06 |
| 9,081,100 | B1 | 7/2015 | Bellinger et al. ........ | G01T 3/08 |
| 9,329,303 | B2 | 5/2016 | Inanc et al. ............ | G01V 5/107 |
| 9,395,454 | B2 | 7/2016 | Orava et al. ............. | G01T 3/06 |
| 9,442,202 | B2 | 9/2016 | Tanner et al. ............ | G01T 3/00 |
| 9,638,813 | B2 * | 5/2017 | Stowe ...................... | C30B 29/46 |
| 9,678,229 | B2 | 6/2017 | Neyland ................. | G01T 3/008 |
| 9,778,392 | B2 | 10/2017 | Justus et al. ......... | G01V 5/0091 |
| 9,817,138 | B2 | 11/2017 | McGregor et al. ..... | G01T 3/008 |
| 9,910,170 | B1 | 3/2018 | Billiard et al. ......... | G01T 3/02 |
| 9,939,538 | B2 | 4/2018 | Ing et al. ............... | G01T 3/065 |
| 9,958,561 | B2 | 5/2018 | Bellinger et al. ....... | G01T 3/065 |
| 9,978,384 | B2 | 5/2018 | Li et al. .................. | G01L 19/04 |
| 10,024,986 | B2 | 7/2018 | Lennert et al. ......... | G01T 3/008 |
| 10,564,112 | B2 | 2/2020 | Zreda et al. ........... | G01N 23/005 |
| 10,845,318 | B2 | 11/2020 | Zreda et al. ........... | G01N 23/005 |
| 10,890,677 | B2 * | 1/2021 | Larue .................... | A01G 25/167 |
| 11,063,553 | B2 * | 7/2021 | Poivet .................... | H02S 30/10 |
| 11,249,036 | B2 * | 2/2022 | Zreda .................... | G01N 33/246 |
| 11,474,048 | B2 * | 10/2022 | Zreda ..................... | G01T 7/005 |
| 2001/0046274 | A1 | 11/2001 | Craig et al. ................ | 376/154 |
| 2003/0012324 | A1 | 1/2003 | Haruyama ................... | 376/159 |
| 2004/0061047 | A1 | 4/2004 | Bolozdynya et al. ....... | 250/251 |
| 2006/0023828 | A1 | 2/2006 | McGregor et al. ......... | 376/158 |
| 2006/0138340 | A1 | 6/2006 | Ianakiev et al. .......... | 250/390.01 |
| 2008/0210880 | A1 | 9/2008 | Baroni et al. ............ | 250/390.11 |
| 2011/0180718 | A1 | 7/2011 | Luszik-Bharda et al. .................... 250/390.03 | |
| 2013/0341519 | A1 | 12/2013 | Li et al. ..................... | G01T 3/06 |
| 2014/0158893 | A1 | 6/2014 | Platt et al. .............. | G01T 3/085 |
| 2014/0158895 | A1 | 6/2014 | Wang et al. ............ | G01T 3/008 |
| 2014/0361187 | A1 | 12/2014 | Zhao et al. ............... | G01T 3/06 |
| 2015/0014234 | A1 | 1/2015 | Early et al. ............ | B65D 90/10 |
| 2015/0241577 | A1 | 8/2015 | Spillane et al. .......... | G01T 3/00 |
| 2015/0355345 | A1 | 12/2015 | Neyland ................. | G01T 3/008 |
| 2016/0356901 | A1 | 12/2016 | Shao et al. ............... | G01T 3/08 |
| 2017/0023684 | A1 | 1/2017 | Inglis et al. ............. | G01T 3/008 |
| 2017/0059723 | A1 | 3/2017 | Ing et al. ................ | G01T 3/065 |
| 2017/0090049 | A1 | 3/2017 | Ramsden et al. ......... | G01T 3/06 |
| 2017/0184736 | A1 | 6/2017 | Ramsden et al. ......... | G01T 3/06 |
| 2017/0247737 | A1 | 8/2017 | Gundry et al. .......... | C12Q 1/06 |
| 2018/0299570 | A1 | 10/2018 | Degtiarenko ............. | G01T 7/00 |
| 2018/0341032 | A1 | 11/2018 | Larue ....................... | G01T 3/00 |
| 2019/0178818 | A1 | 6/2019 | Zreda et al. ........... | G01N 23/00 |
| 2020/0036325 | A1 | 1/2020 | Poivet .................... | H02S 30/10 |
| 2021/0102906 | A1 | 4/2021 | Zreda et al. ........... | G01N 23/09 |

OTHER PUBLICATIONS

Desilets, D., and M. Zreda, 2013. Footprint diameter for a cosmic-ray soil moisture probe: Theory and Monte Carlo simulations. Water Resources Research 49, 3566-3575, doi: 10.1002/wrcr.20187 (10 pgs).

Desilets et al., "Nature's neutron probe: Land surface hydrology at an elusive scale with cosmic rays", Water Resources Research, vol. 46, No. 11, Nov. 1, 2010, 7 pgs.

Dhairyawan et al., "Response Functions of Spherically Moderated Neutron Detectors", Nuclear Instruments and Methods, vol. 169, No. 1, Feb. 1980, pp. 115-120.

Fragopoulou et al. Shielding around spallation neutron sources, Journal of Physics: Conference Series vol. 41, pp. 514-581 (Year: 2006).

Heidbüchel et al., "Use of cosmic-ray neutron sensors for soil moisture monitoring in forests" *Hydrol. Earth Syst. Sci.*, 20, 1269-1288, 2016.

"Insights into the footprint of the cosmic-ray probe from new field measurements and neutron modeling," Cosmos 5 Workshop, Copenhagen, Aug. 22-24, 2016 (63 pgs).

Knoll, G.F., 2000, Radiation detection and measurement: New York, Wiley, 802 p. (82 pgs), relevant pp. 55-57, 159-173 and 505-520.

Köhli, M., M. Schrön, M. Zreda, U. Schmidt, P. Dietrich, and S. Zacharias, 2015. Footprint characteristics revised for field-scale soil moisture monitoring with cosmic-ray neutrons. Water Resources Research 51, 5772-5790 (20 pgs).

Lab C Website, www.lab-c.co (7 pgs), dated Dec. 18, 2018.

Rees, et al., "Optimizing moderation of He-3 neutron detectors for shielded fission sources", Nuclear Instruments and Methods in Physics Research, vol. 691, Jul. 2012, pp. 72-80.

Schrön, M., M. Köhli, L. Scheiffele, J. Iwema, H.R. Bogena, L. Lv, E. Martini, G. Baroni, R. Rosolem, J. Weimar, J. Mai, M. Cuntz, C. Rebmann, S.E. Oswald, P. Dietrich, U. Schmidt, and S. Zacharias, 2017b. Improving calibration and validation of cosmic-ray neutron sensors in the light of spatial sensitivity. Hydrology and Earth System Sciences 21, 5009-5030 (22 pgs). Published Oct. 6, 2017.

Schrön, M., Zacharias, S., Womack, G., Köhli, M., Desilets, D., Oswald, S. E., Bumberger, J., Mollenhauer, H., Kögler, S., Remmler, P., Kasner, M., Denk, A., and Dietrich, P., 2017a. Intercomparison of Cosmic-Ray Neutron Sensors and Water Balance Monitoring in an Urban Environment, Geoscientific Instruments, Methods and Data Systems Discussions, https://doi.org/10.5194/gi-2017-34, in review (18 pgs). Published Mar. 9, 2018.

Schrön et al., "Monitoring Environmental Water with Ground Albedo Neutrons and Correction for Incoming Cosmic Rays with Neutron Monitor Data", Proceedings of Science, 34th International Cosmic Ray Conference, Jul. 30-Aug. 6, 2015, accessed by EP Examiner on Sep. 2, 2021 at: https://inspirehep.net/files/3062ae9e5e19a266535c5147bc2f3b5f, 8 pgs.

Yamashita, et al., "Detection Efficiency of Bare and Moderated BF3-Gas-Filled Proportional Counters for Isotropic Neutron Fluxes",

(56) References Cited

OTHER PUBLICATIONS

Journal of Nuclear Science and Technology, vol. 3, No. 8, Aug. 1966, pp. 343-353.

Zreda, M., D. Desilets, T.P.A. Ferré, and R.L. Scott, 2008. Measuring soil moisture content non-invasively at intermediate spatial scale using cosmic-ray neutrons. Geophysical Research Letters 35, L21402, doi: 10.1029/2008GL035655 (5 pgs).

Zreda, M., W.J. Shuttleworth, X. Zeng, C. Zweck, D. Desilets, T. Franz, and R. Rosolem, 2012. COSMOS: the COsmic-ray Soil Moisture Observing System. Hydrology and Earth System Sciences 16, 4079-4099 (23 pgs).

Zreda et al., "Cosmic-ray neutron probe: non-invasive measurement of soil water content", Dept. of Hydrology and Water Resources, Univ. of Arizona, undated, accessed by EP Examiner on Sep. 2, 2021 at: http://quebec.hwr.arizona.edu/research/agu05-zreda-cosmic-ray-neutron-probe.pdf, 1 pg.

Zreda et al., "COSMOS: the COsmic-ray Soil Moisture Observing System", Hydrology and Earth System Sciences, vol. 16, Nov. 7, 2012, 21 pgs.

European Search Report issued in EP Application No. 18 885 680.1, dated Jul. 20, 2021, 14 pgs.

European Search Report issued in EP Application No. 18 887 019.0, dated Sep. 2, 2021, 13 pgs.

International Preliminary Report on Patentability issued in PCT/US18/64548 dated Jun. 9, 2020 (8 pgs).

International Preliminary Report on Patentability issued in PCT/US18/64573 dated Jun. 9, 2020 (6 pgs).

International Search Report and Written Opinion issued in PCT/US2018/064548 dated Feb. 19, 2019, 11 pgs.

International Search Report and Written Opinion issued in PCT/US2018/064573 dated Feb. 14, 2019, 9 pgs.

Office Action issued in U.S. Appl. No. 16/213,812 dated Feb. 15, 2019, 20 pgs.

Office Action issued in U.S. Appl. No. 16/213,812 dated Aug. 16, 2019 (16 pgs).

Office Action issued in U.S. Appl. No. 16/213,741 dated Feb. 8, 2019, 9 pgs.

Office Action issued in U.S. Appl. No. 16/213,741 dated Mar. 7, 2019, 18 pgs.

Office Action issued in U.S. Appl. No. 16/213,741 dated Jul. 9, 2019, 22 pgs.

Office Action issued in U.S. Appl. No. 16/213,741 dated Jan. 14, 2020, 18 pgs.

Office Action issued in U.S. Appl. No. 16/213,741 dated Mar. 3, 2020, 11 pgs.

Notice of Allowance issued in U.S. Appl. No. 16/213,812, dated Oct. 8, 2019, 6 pages.

Notice of Allowance issued in U.S. Appl. No. 16/213,741, dated Jul. 20, 2020. 9 pages.

Notice of Allowance issued in U.S. Appl. No. 17/102,118, dated Oct. 13, 2021, 16 pgs.

European Search Report issued in EP Application No. 22 165 845.3 dated Jun. 22, 2022, 14 pgs.

European Search Report issued in EP Application No. 22 171 348.0 dated Aug. 16, 2022, 8 pgs.

European Search Report issued in EP Application No. 21 209 958.4 dated Mar. 21, 2022, 10 pgs.

European Search Report issued in EP Application No. 18 885 680.1 dated May 17, 2022, 11 pgs.

Stevanato et al., "Towards the optimization of a scintillator-based neutron detector for large non-invasive soil moisture estimation", IEEE International Workshop on Metrology for Agriculture and Forestry, Nov. 4, 2020, 5 pgs.

Notice of Allowance issued in U.S. Appl. No. 17/307,827, dated Jun. 15, 2022, 19 pgs.

International Search Report and Written Opinion issued in PCT/US21/54591 dated Nov. 30, 2021, 9 pgs.

\* cited by examiner

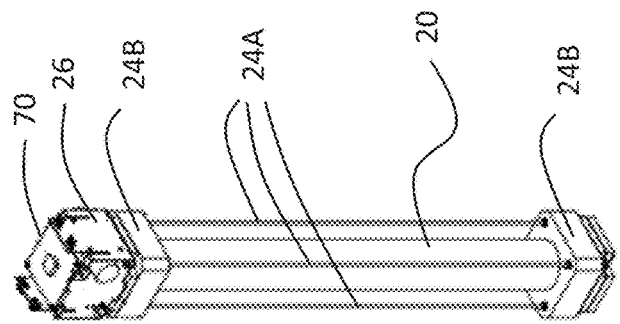
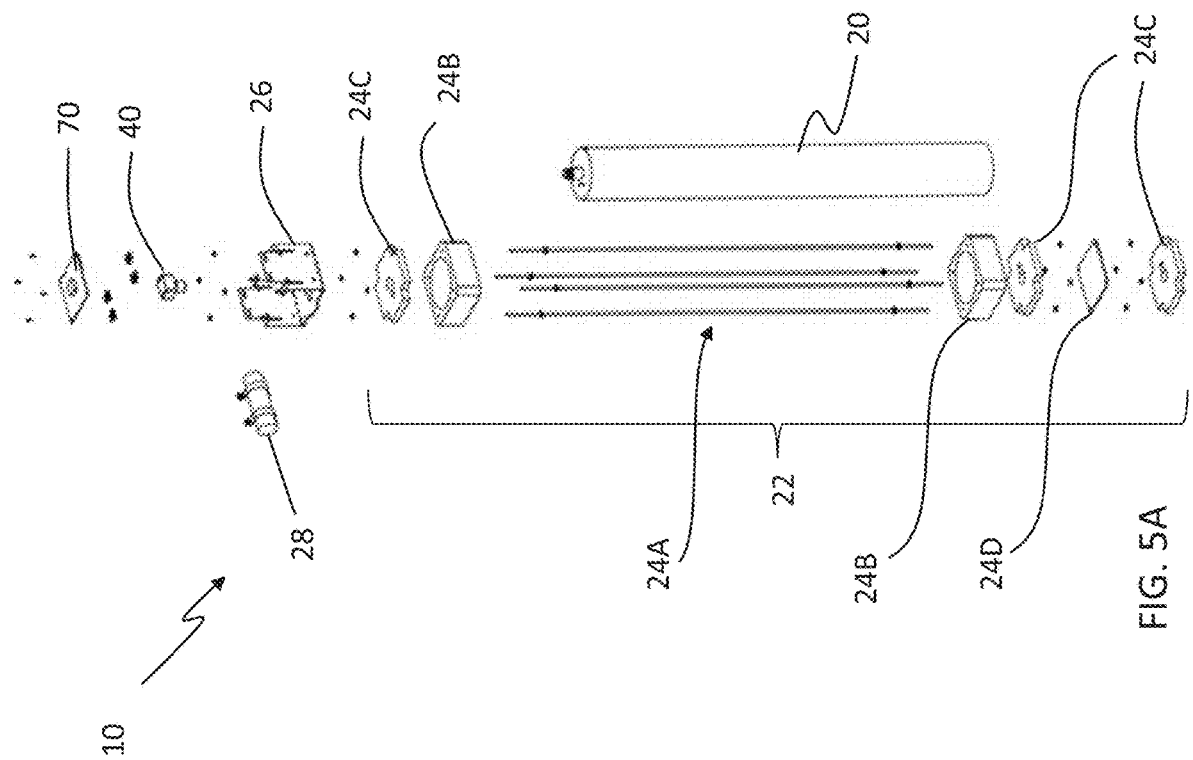

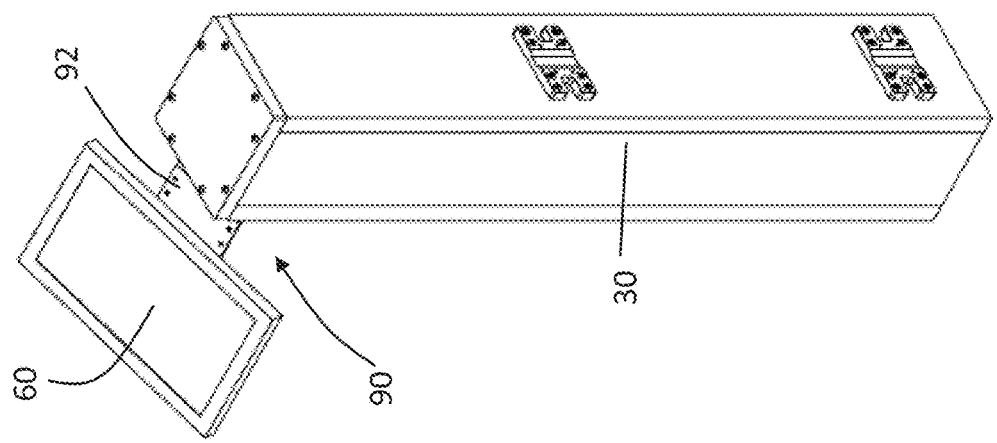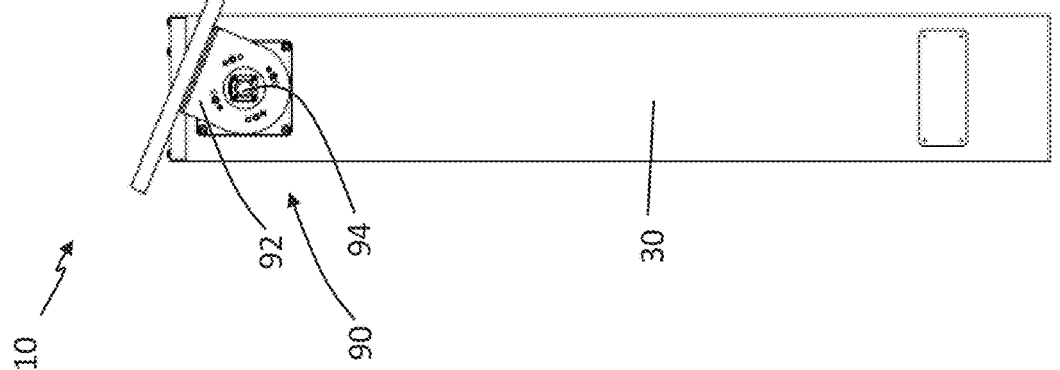

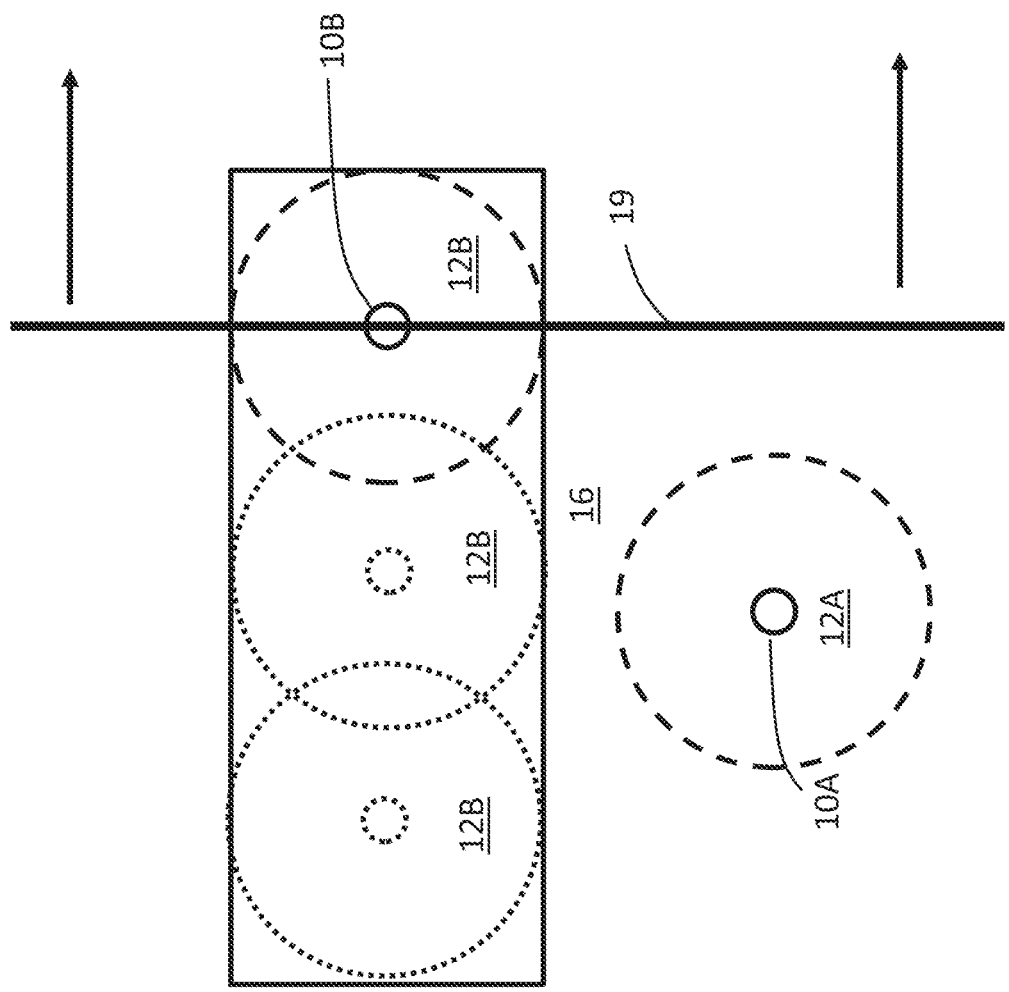
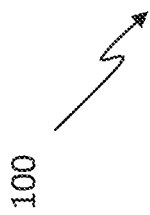
FIG. 13

SYSTEMS AND METHODS FOR COSMOGENIC NEUTRON SENSING MOISTURE DETECTION IN AGRICULTURAL SETTINGS

CROSS REFERENCE TO RELATED APPLICATION

This application claims benefit of U.S. Provisional Application Ser. No. 63/090,596 entitled, "Cosmic ray soil moisture measurement (CRS) systems for use in commercial settings" filed Oct. 12, 2020, the entire disclosure of which is incorporated herein by reference.

FIELD OF THE DISCLOSURE

The present disclosure is generally related to cosmogenic neutron sensing and more particularly is related to systems and methods for cosmogenic neutron sensing moisture detection in agricultural settings.

BACKGROUND OF THE DISCLOSURE

Measuring the moisture content of materials such as surface soils using cosmogenic neutron detection is known in the art. Cosmic rays continually bombard the Earth and penetrate into materials at the land surface, including soil, atmosphere, water, man-made structures, vegetation, and the like. Inside these materials, cosmogenic high-energy (>10 MeV) neutrons collide with matter and produce fast (<2 MeV) cosmogenic neutrons. These neutrons interact with matter in reactions called neutron scattering that lead to the gradual decrease of neutron energies and eventually to the removal of neutrons from the environment. Hydrogen is by far the most efficient element in scattering neutrons. Therefore, moisture content of the soil through which neutrons have traveled can be inferred from the measured neutron flux, which is inversely correlated with soil moisture content. This principle has been used to develop cosmogenic neutron soil moisture measuring systems and methods which are used around the world.

In recent times, cosmogenic neutron soil moisture measuring systems have been used in academic and government research fields to conduct experimentation with the detection of soil moisture in various locations for various purposes. While initial experiments have been conducted, these trials do not account for the shortcomings of these systems to provide practical and commercially viable soil moisture monitoring to the agricultural community.

Thus, a heretofore unaddressed need exists in the industry to address the aforementioned deficiencies and inadequacies.

SUMMARY OF THE DISCLOSURE

Embodiments of the present disclosure provide an apparatus for cosmogenic neutron sensing to detect moisture. Briefly described, in architecture, one embodiment of the system, among others, can be implemented as follows. An apparatus for cosmogenic neutron sensing to detect moisture includes a thermal neutron proportional counter. A housing is formed at least partially from a moderating material, which is positioned around the thermal neutron proportional counter. A proportional counter electronics unit is within the housing and has a preamplifier and a shaping amplifier. The preamplifier and shaping amplifier are directly connected to the thermal neutron proportional counter. At least one photovoltaic panel provides electrical power to the thermal neutron proportional counter. A data logger is positioned vertically above the thermal neutron proportional counter and proportional counter electronics unit. A signal from the thermal neutron proportional counter is transmitted through the proportional counter electronics unit and is received by the data logger. The signal indicates a moisture content within a measurement surface of the thermal neutron proportional counter.

The present disclosure can also be viewed as providing a system for cosmogenic neutron sensing to detect moisture in an agricultural location. Briefly described, in architecture, one embodiment of the system, among others, can be implemented as follows. The system for cosmogenic neutron sensing to detect moisture in an agricultural location includes a non-contacting, field-scale cosmogenic neutron sensor for measuring soil moisture in a measurement surface. The cosmogenic neutron sensor has a thermal neutron proportional counter. A housing is formed at least partially from a moderating material, wherein the moderating material is positioned around the thermal neutron proportional counter. A proportional counter electronics unit is within the housing and has a preamplifier and a shaping amplifier, wherein the preamplifier and shaping amplifier are directly connected to the thermal neutron proportional counter. At least power source provides electrical power to the thermal neutron proportional counter. A data logger is positioned vertically above the thermal neutron proportional counter and proportional counter electronics unit, wherein a signal from the thermal neutron proportional counter is transmitted through the proportional counter electronics unit and is received by the data logger, wherein the signal indicates a moisture content within a measurement surface of the thermal neutron proportional counter. An agricultural irrigation device has at least one frame member, wherein the cosmogenic neutron sensor is mounted to the at least one frame member, wherein the cosmogenic neutron sensor is positioned a spaced distance above a ground surface.

The present disclosure can also be viewed as providing methods of manufacturing an apparatus for cosmogenic neutron sensing to detect moisture. In this regard, one embodiment of such a method, among others, can be broadly summarized by the following steps: sensing to detect moisture; providing a thermal neutron proportional counter; positioning the thermal neutron proportional counter within a housing formed at least partially from a moderating material, wherein the moderating material is positioned around the thermal neutron proportional counter; positioning a proportional counter electronics unit within the housing, the proportional counter electronics unit having a preamplifier and a shaping amplifier, wherein the preamplifier and shaping amplifier are directly connected to the thermal neutron proportional counter; providing electrical power to the thermal neutron proportional counter with at least one photovoltaic (PV) panel; and receiving a signal from the thermal neutron proportional counter in a data logger positioned vertically above the thermal neutron proportional counter, wherein the signal is transmitted through the proportional counter electronics unit before being received by the data logger, wherein the signal indicates a moisture content within a measurement surface of the thermal neutron proportional counter.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 5A-5B are exploded and non-exploded view illustrations of the apparatus for cosmogenic neutron sensing of FIG. 1, in accordance with the first exemplary embodiment of the present disclosure.

FIGS. 8A-8C are illustrations of the apparatus for cosmogenic neutron sensing of FIG. 1 with an external PV panel mount, in accordance with the first exemplary embodiment of the present disclosure.

FIGS. 12-13 are diagrammatic illustrations of the system for cosmogenic neutron sensing to detect moisture of FIG. 9, in accordance with the first exemplary embodiment of the present disclosure.

DETAILED DESCRIPTION

Figure 1:
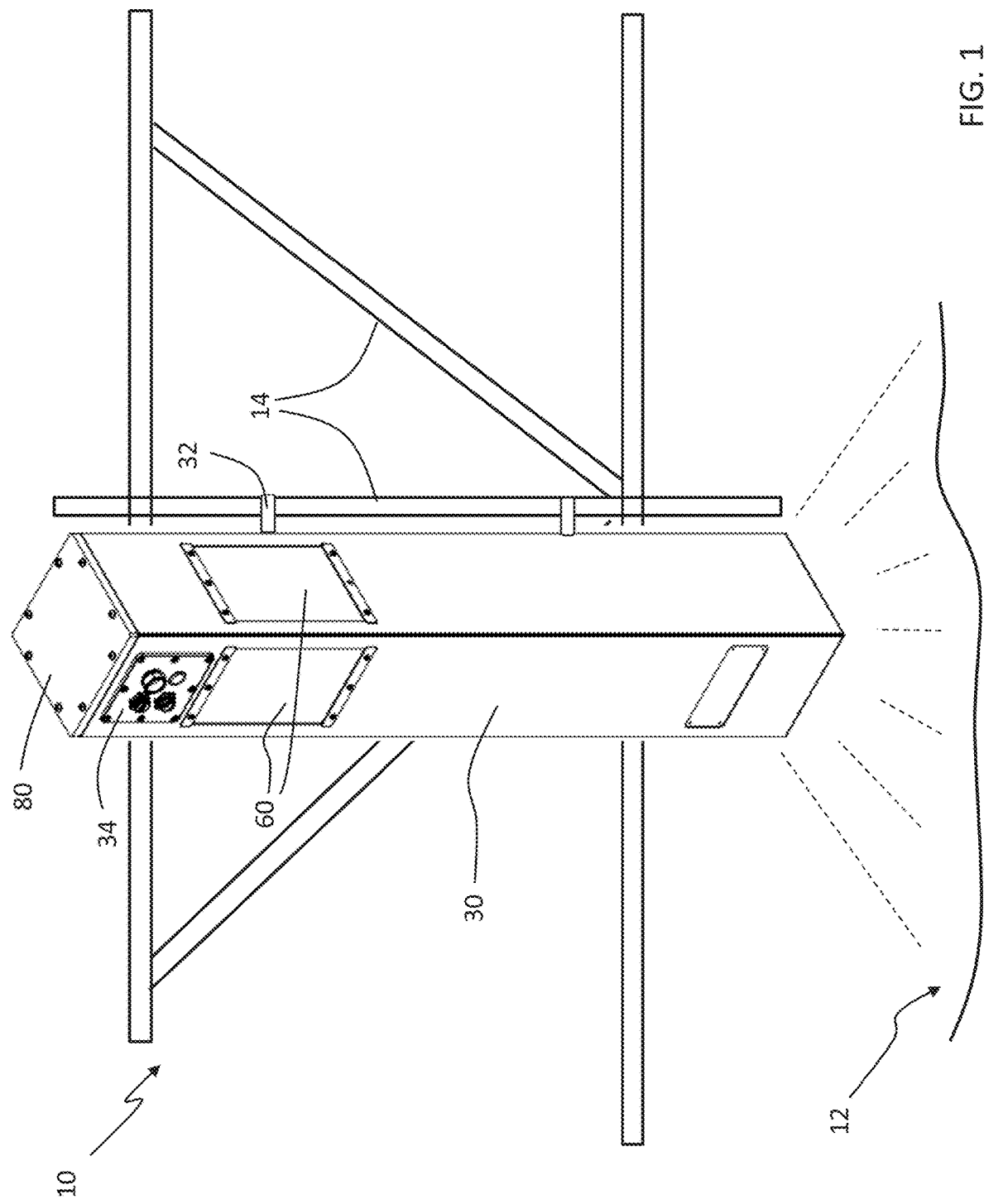
FIG. 1 is an illustration of an apparatus for cosmogenic neutron sensing, in accordance with a first exemplary embodiment of the present disclosure.
Figure 3:
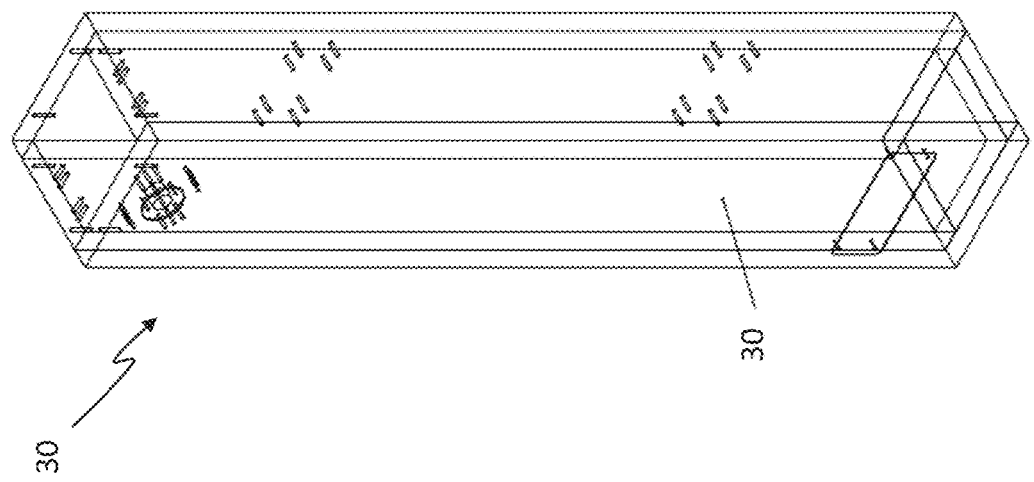
FIGS. 2-4 are various illustrations of the apparatus for cosmogenic neutron sensing of FIG. 1, in accordance with the first exemplary embodiment of the present disclosure.
Figure 2:
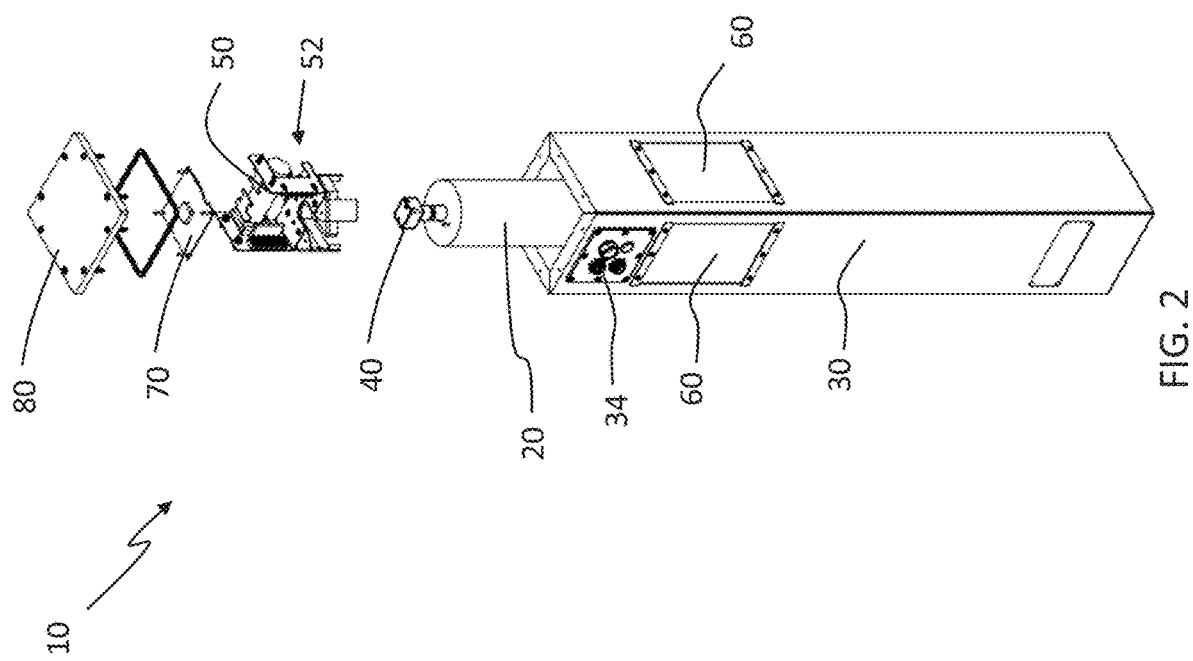
Figure 4:
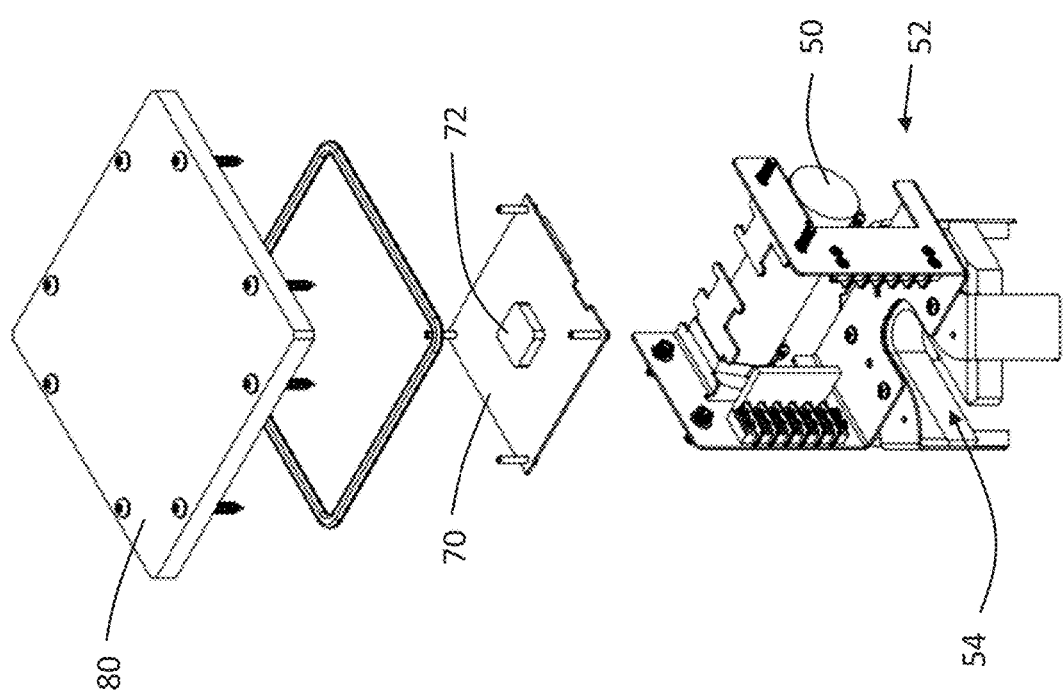

To provide solutions to the use of cosmogenic neutron sensing to detect moisture within agricultural settings, the present disclosure is directed to an apparatus for cosmogenic neutron sensing to detect moisture. FIG. 1 is an illustration of an apparatus for cosmogenic neutron sensing 10, in accordance with a first exemplary embodiment of the present disclosure. FIGS. 2-4 are various illustrations of the apparatus for cosmogenic neutron sensing 10 of FIG. 1, in accordance with the first exemplary embodiment of the present disclosure. With reference to FIGS. 1-4, the apparatus for cosmogenic neutron sensing 10, which may be referred to herein simply as 'apparatus 10' includes a thermal neutron proportional counter 20. The thermal neutron proportional counter 20 may include various types of thermal neutron counters, including Helium-3 thermal neutron proportional counters, Boron trifluoride (BF3) thermal neutron proportional counter, Boron-lined (B10) thermal neutron proportional counters, and/or Lithium-6 (metal foil) type thermal neutron counters, scintillators, or other devices with similar functioning among others.

The thermal neutron proportional counter 20 is positioned, at least partially, within a housing 30 which is formed, at least partially, from a moderating material, such as high density polyethylene (HDPE) or a similar material capable of moderating the thermal neutron proportional counter 20. In a preferred example, the housing 30 is manufactured substantially only from the moderating material, which may reduce the size of the apparatus 10 as well as its weight, since additional housing materials, like metals, may not be needed. For instance, when the housing is manufactured from the moderating material, it may alleviate the need for a second enclosure, such as an aluminum outer shell. However, in other examples, the housing 30 may be made from a combination of a moderating material and non-moderating materials, such as, for example, when a substantial portion of the housing 30 is manufactured for moderating material but non-moderating materials like metal are used in locations of the housing 30 which were not required to perform a moderating function. Accordingly, the moderating material may be positioned at least around the thermal neutron proportional counter 20, as well as in other locations on the housing 30.

Together, the thermal neutron proportional counter 20 in the housing 30, which has or is formed from the moderating material, form a cosmogenic neutron sensor capable of detecting moisture within a measurement surface 12, as shown in FIG. 1. The measurement surface 12 may be, for example, a ground surface which contains moisture, and more specifically, within an agricultural setting, such as within a field of crops or another setting in which plants or vegetation are grown either for consumption or for use in another manner. While the apparatus 10 may have uses in a variety of industries, it is particularly intended to be used within the agricultural industry to aid in the detection of moisture within agricultural fields. More specifically, the apparatus 10 may find a particular use with irrigation systems used in agriculture, such as center pivot irrigation systems or linear based irrigation systems which move relative to crop locations to provide irrigation for those crops. As such, the housing 30 may be mountable to frame member 14 of an agricultural irrigation device, such that the apparatus 10 can provide moisture detection over the crops as the agricultural irrigation device is moved. As shown in FIG. 1, this may include the use of a bracket 32 or similar mechanical fastener which can be used to mount the housing 30 to the frame member 14 of the agricultural irrigation device.

As can be seen in FIG. 3, when formed from only a moderating material like HDPE, the housing 30 may be constructed by welding edges of a planer HDPE sheets together, thereby forming a structure having an interior space which can receive the thermal neutron proportional counter 20 as well as other components of the apparatus 10. The resulting structure of the housing may be watertight and airtight at all joints of the HDPE sheets, thereby providing a sound enclosure to contain the electronics of the apparatus 10. The shape of the housing 30 may vary depending on the design and shape of the thermal neutron proportional counter 20. For example, for thermal neutron proportional counter 20 that is cylindrical in shape, a rectangular housing 30 may be used such that the four elongated sides of the housing 30 substantially cover the elongated sidewall of the cylinder of the thermal neutron proportional counter 20. The housing 30 may be designed with other shapes to accommodate thermal neutron proportional counters 20 that are rectangular, square, or have other spatial configurations.

The thermal neutron proportional counter 20 may be located within a lower part of the housing 30 such that it is positioned closest the bottom of the housing 30. The additional components of the apparatus 10 may be positioned above the thermal neutron proportional counter 20, which helps to ensure that these additional components do not obstruct or otherwise influence the cosmogenic neutron sensing which occurs on the measurement surface 12 below the housing 30. The apparatus 10 further includes a proportional counter electronics unit 40 which is positioned within the housing 30. The proportional counter electronics unit 40 has at least a preamplifier and a shaping amplifier, among other components, which are contained within a metal enclosure or manifold. The proportional counter electronics unit 40 include a high voltage supply to provide power to the thermal neutron proportional counter 20 through the high voltage connector on one end of the thermal neutron proportional counter 20, or it may be possible for that high voltage supply to be located elsewhere. The proportional counter electronics unit 40 is mounted to the thermal neutron proportional counter 20 such that the preamplifier and shaping amplifier are directly connected to the thermal neutron proportional counter 20, as shown in FIG. 2. Attachment of the preamplifier directly to the thermal neutron proportional counter 20 may reduce a significant source of vibrational noise in the signal received from the thermal neutron proportional counter 20. The signal emitted from the proportional counter electronics unit 40 to the data logger 70 PCB is amplified and not subject to noise pickup from environmental RF while it is being transmitted to the data logger 70.

To provide power to the apparatus 10, at least one power source, such as a battery 50 or a supercapacitor may be used to provide electrical power to the thermal neutron proportional counter 20 and other components of the apparatus 10. The battery 50, when used, may be mounted to a bracket assembly 52 which is mounted to the top of the thermal neutron proportional counter 20. FIG. 4 is an exploded view illustration of a top portion of the apparatus for cosmogenic neutron sensing 10 of FIG. 1, in accordance with the first exemplary embodiment of the present disclosure, and in particular, it depicts a detailed view of the bracket assembly 52. As shown in FIG. 4, bracket assembly 52 includes a lower portion which substantially connects to a top of the thermal neutron proportional counter 20, and in particular to a bracket holding the thermal neutron proportional counter 20, as discussed more relative to FIG. 4. The bracket assembly 52 also has slot 54 which allows the proportional counter electronics unit 40 to be positioned within an interior of the bracket assembly 52. In this position the proportional counter electronics unit 40 is located proximate to the battery 50, and proximate to additional circuitry in electronics which can be mounted to the top of the bracket assembly 52.

The battery 50 may be powered by a variety of power sources, including traditional grid power or an off grid power source. In a preferred example the battery 50 is provided power using one or more photovoltaic (PV) panels 60 which converts sunlight into electrical energy to power the battery 50 which in turn provides power to the electrical components of the apparatus 10. The use of PV panels 60 may be particularly beneficial for the apparatus 10 since it is traditionally used in a remote agricultural setting, and moving within an agricultural irrigation device, such as a center pivot irrigation system. As shown in FIGS. 1-2, there may be a plurality of PV panels 60 used, where the PV panels 60 are positioned on a plurality of sides of the housing 30, or integrated within the sidewalls forming the housing 30. The PV panels 60 are integrated within the sidewalls forming the housing 30, a translucent window or similar structure may allow sunlight through the housing 30 and into the PV panels 60. Since some moderating materials are translucent, the translucent window, if used, may not detract from the moderating function of the moderating materials within the housing 30. For instance, the translucent window could be a thin layer of semi translucent moderating material instead of a traditional glass or plexiglass material. In other designs, the PV panel 60 may be mounted to the exterior of the moderating housing 30, and a wired connection may extend into the housing 30 to convey electrical power to the battery 50. It is noted that in place of a battery 50, the apparatus 10 may function with one or more PV panels 60 providing electrical power to a supercapacitor which in turn powers the components of the apparatus 10.

The use of PV panels 60 on a plurality of sides of the housing 30, such as on four sides of the housing 30, as shown in FIG. 1, permits the gathering of substantial sunlight for all azimuthal angles. For example, when the apparatus 10 is positioned on a center pivot irrigation system, it will rotate around the central point of the irrigation system, such that the position of the sun relative to housing 30 will change continually as the center pivot irrigation system rotates 360 degrees. By placing a plurality PV panel 60 on different sides of the housing 30, it can be insured that at least one of the PV panels 60 will receive sunlight irrespective of the radial position of the center pivot irrigation system. In other designs, the housing 30 may have a PV panel 60 located on a top surface of the housing 30, such that the PV panel 60 is substantially facing upwards irrespective of a radial position of the center pivot irrigation system. Additional designs for placement and mounting of the PV panel 60 or PV panels 60 is also discussed relative to FIGS. 8A-8B.

The apparatus 10 may further include a data logger 70 with a communications modem, antenna, and battery, among other components. As shown in FIGS. 2 and 4, the data logger 70 may be mountable to the bracket assembly 52, such that it is positioned vertically above the thermal neutron proportional counter 20 and proportional counter electronics unit 40, which helps ensure that the signals emitted and received by the data logger 70 are not obstructed by the thermal neutron proportional counter 20 or other components of the apparatus 10. In particular, positioning the data logger 70 near the top of the apparatus 10, with only the plastic cover 80 above it, may help ensure that the antenna of the data logger 70 has a substantially unobstructed line of sight to the sky, which increases the chance of the antenna successfully connecting to a satellite or a cell tower. The data logger 70 may be used to transmit data between the remote location of the housing 30 and another location, such as a control center located off site. As shown in the figures, the data logger 70 may be constructed from a printed circuit board (PCB) which is miniaturized to fit in an all-in-one enclosure.

The data logger 70 may have a ground plane below a communications antenna 72 that faces upward toward plastic lid 80, where the ground plane in plastic lid 80 enhances the function of the antenna 72. The antenna 72 may include any type of communications device, such as cellular, satellite, or generic radio communications. Additionally, the data logger 70 further includes near proximity communication mediums, such as Bluetooth to provide wireless communication with Bluetooth enabled devices in the local vicinity and plug in communication capabilities such as with USB communication. Any type of local or remote communication protocol may be used with the apparatus 10. For communication which requires a physical connection, a feedthrough connector 34 may be provided on the housing 30, such that one can access the interior electronic components up the apparatus 10 from an exterior location of the housing 30.

The data logger 70 may also include additional components in functionality to help operate the apparatus 10. For example, the data logger 70 may also have an integrated solar charge controller to control charging of the internal battery 50 by the PV panel 60. It may further control the electrical power parameters or powering thermal neutron proportional detector 20 as well as the proportional counter electronics unit 40, such as by supplying high voltage power to the thermal neutron proportional detector 20 in low voltage power to the proportional counter electronics unit 40. The data logger 70 may have a low power design which uses computational algorithms to perform functions required by the apparatus 10. It may also have a multichannel analyzer (MCA).

In use, signals from thermal neutron proportional detector 20 better indicative of soil moisture within a measurement surface 12 may be transmitted to the proportional counter electronics unit 40. Those signals may be processed within the proportional counter electronics unit 40 then transmitted to the data logger 70, where signals may be emitted beyond the apparatus 10, such as to a control unit or the resulting data can be further analyzed, displayed, or provided to a user as needed.

The mounting of the thermal neutron proportional detector 20 is discussed in detail relative to FIGS. 5A-5B, which are an exploded and non-exploded view illustration of the apparatus for cosmogenic neutron sensing 10 of FIG. 1, in accordance with the first exemplary embodiment of the present disclosure. In particular, FIGS. 5A-5B illustrate a custom frame structure 22 which is used to mount the thermal neutron proportional detector 20 within the housing 30 in such a manner to cushion and reduce vibrational noise in the thermal neutron proportional detector 20. The custom frame structure 22 includes a plurality of threaded rods 24A which may be positioned about the sides of the thermal neutron proportional detector 20. Insertable sleeves 24B are positionable on the ends of the threaded rods 24A, where the insertable sleeves 24B are constructed from a vibration reducing material, such as foam or rubber, which limits vibrational forces from transferring between the housing 30 and the thermal neutron proportional detector 20.

The insertable sleeves 24B may have holes which receive ends of the threaded rods 24A, and a larger, centrally located whole which may receive the ends of the thermal neutron proportional detector 20. On opposing sides of the insertable sleeves 24B, one or more vibrational reducing bottom pieces 24C may be located, which may be constructed from the same materials as the insertable sleeves 24B. Additionally, along the bottom side, a plate 24D may be sandwiched between two vibrational reducing bottom pieces 24C. Together, these structures effectively reduce vibrational coupling between the thermal neutron proportional detector 20 and the housing 30.

At the top of the assembly, a bracket 26 is mountable to the tops of the threaded rods 24A to hold the components above the thermal neutron proportional detector 20. The bracket 26 includes features to allow a battery 28 to be mounted to the bracket 26. The mounting arrangement of the battery 28 to the bracket 26 may include one or more battery clamps which retain the battery 28 in place. As shown in FIG. 5A, the proportional counter electronics unit 40 may be mounted to the top of the bracket of the manifold, and the data logger 70 is then mountable above the proportional counter electronics unit 40. These vibration reducing inserts extend beyond the metal frame formed by the threaded rods 24A such that only these inserts touch the walls of the housing 30 when the assembly is inserted into the housing 30. As such, the entire assembly, including the thermal neutron proportional detector 20, the electronic components, and the battery, are cushioned. The assembled view of the components is depicted in FIG. 5B. While one example of the assembly is depicted in the figures and described herein, it is noted that these mounting components may vary depending on the size and shape up of the thermal neutron proportional detector 20 and the other components of the apparatus 10.

Figure 7:
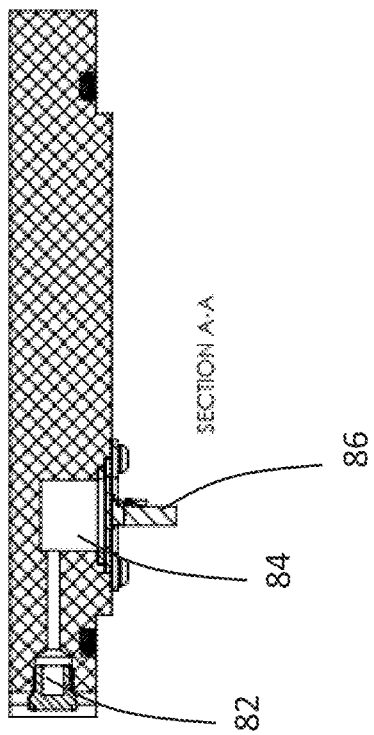
FIGS. 6-7 are an exploded view illustration, and non-exploded cross-sectional view illustration along the line A-A, respectively, of the apparatus for cosmogenic neutron sensing of FIG. 1, in accordance with the first exemplary embodiment of the present disclosure.
Figure 6:
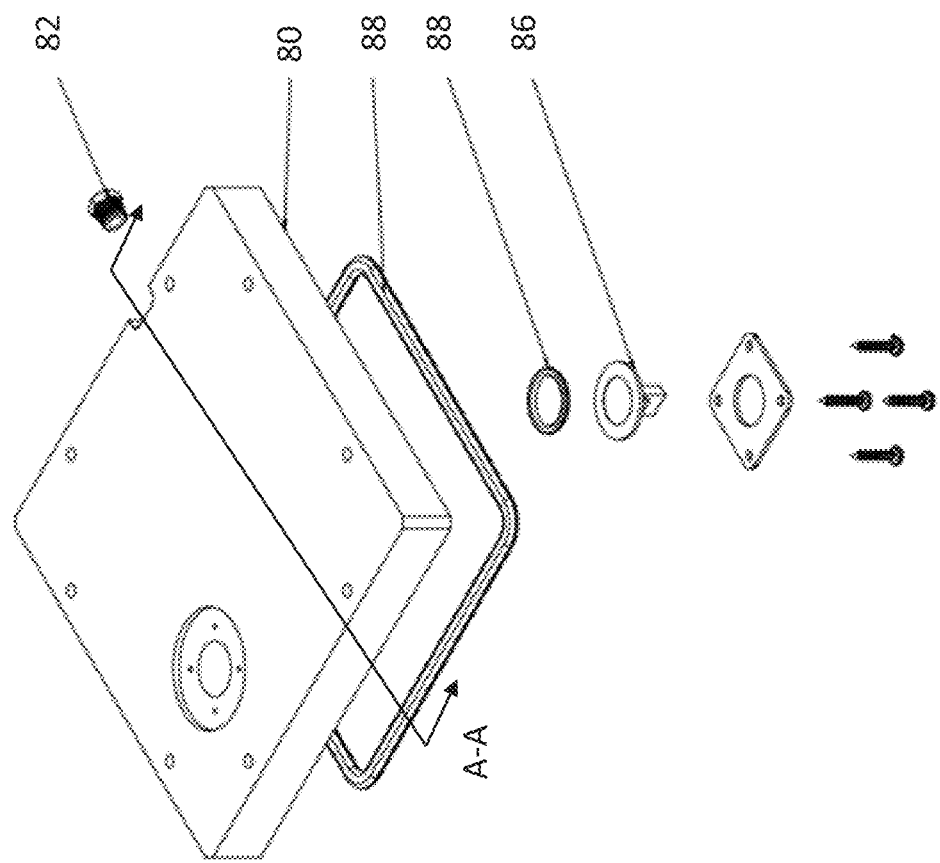

FIGS. 6-7 are an exploded view illustration, and non-exploded cross-sectional view illustration along the line A-A, respectively, of the apparatus for cosmogenic neutron sensing 10 of FIG. 1, in accordance with the first exemplary embodiment of the present disclosure. FIGS. 6-7 depict the lid 80 of the apparatus 10. The lid 80 may be constructed from a plastic material which allows RF signals from the antenna on the top of data logger 70 to penetrate the lid 80 and reach cellular towers or satellites. The lid 80 also has a penetration with a breather valve 82 that connects to a cavity 84 in the lid 80 which allows exposure to the environment of sensor 86. The sensor 86 may be a PCB which has temperature and humidity sensing capabilities which are used for diagnostic purposes, such as monitoring the electronics components inside the housing 30, and for monitoring the humidity and pressure to measure environmental parameters for device calibration. The sensor 86 and the lid 80 may be sealed with one or more gaskets or O-ring structures 88 to protect the interior of the enclosure from exposure to the environment.

FIGS. 8A-8C are illustrations of the apparatus for cosmogenic neutron sensing 10 of FIG. 1 with an external PV panel mount, in accordance with the first exemplary embodiment of the present disclosure. As shown in FIGS. 8A-8C, instead of a PV panel 60 being integrated within the housing 30, as discussed previously, it is also possible to mount the PV panel 60 on a movable mount 90 which is exterior of the housing 30. The movable mount 90 may include an arm 92 which extends from the housing 30 and is connected to a motor or actuator 94 within or attached to the housing 30. The mount 90 may be rotationally movable such that a PV panel 60 which is carried on an end of the arm 92 can be oriented to the desired position relative to sunlight. This particular arrangement may be beneficial if the apparatus is installed in a stationary irrigation system. When the apparatus 10 with the movable PV panel 60 mount is used in a moveable irrigation system, it may be possible to simply orient PV panel 60 directly upright such that it can receive the desired sunlight regardless of its position. In other examples, it is possible to have a mount without an electromechanical actuator, whereby the mount can be manually set in place or oriented in a particular position by the user.

As can be understood, the apparatus 10 as described herein may allow for all components to be substantially enclosed within a single enclosure which is weatherproof and capable of being used in most environmental conditions. While cosmogenic neutron sensing systems have been used in the past for moisture monitoring, they conventionally are made from multiple discrete components including the sensor, a controller/logger and battery in a separate enclosure, with external antennas and solar panels. Conventionally, these various components are individually mounted on a pole and connected together via cables, but the cables have commonly been a point of failure in the system, sometimes being destroyed by weather or animals. Thus, the apparatus 10 is capable of providing benefits to the field of cosmogenic neutron sensing within the agricultural industry.

It is further noted that a benefit of the apparatus 10 is that it is a non-contacting, field-scale device which is capable of measuring average soil moisture over a wide area. Conventionally, cosmogenic neutron sensors have largely been used in academic and government research applications applied to large scale hydrological features such as flood plains and watersheds. Commercial applications that require knowledge of soil moisture can benefit from the cosmogenic neutron sensing technology. The non-contacting nature of the apparatus 10 means that it does not need to be inserted into the ground or even touch the ground. This is a benefit in applications where in-ground sensors and wires would be problematic. For example, in an agricultural setting where equipment must drive over a field for planting or harvesting, in-ground sensors and cables can get in the way and obstruct the farming machinery. Another benefit of the non-contacting property is that the sensor can collect data while moving, and as such, it can be used in mobile as well as stationary applications. Because the apparatus 10 is field-scale, it is capable of measuring the average soil moisture over a large region around where it is located, on the order of hundreds of meters radially, and to a depth of 70 cm or more, and averages over soil moisture in homogeneities on this scale.

While FIGS. 1-8C describe the apparatus 10, the apparatus 10 may be used as part of a system for cosmogenic neutron sensing to detect moisture, as well as in various different methods of detecting moisture within an agricultural setting. FIGS. 9-18 illustrate aspects of this system or method.

Figure 9:
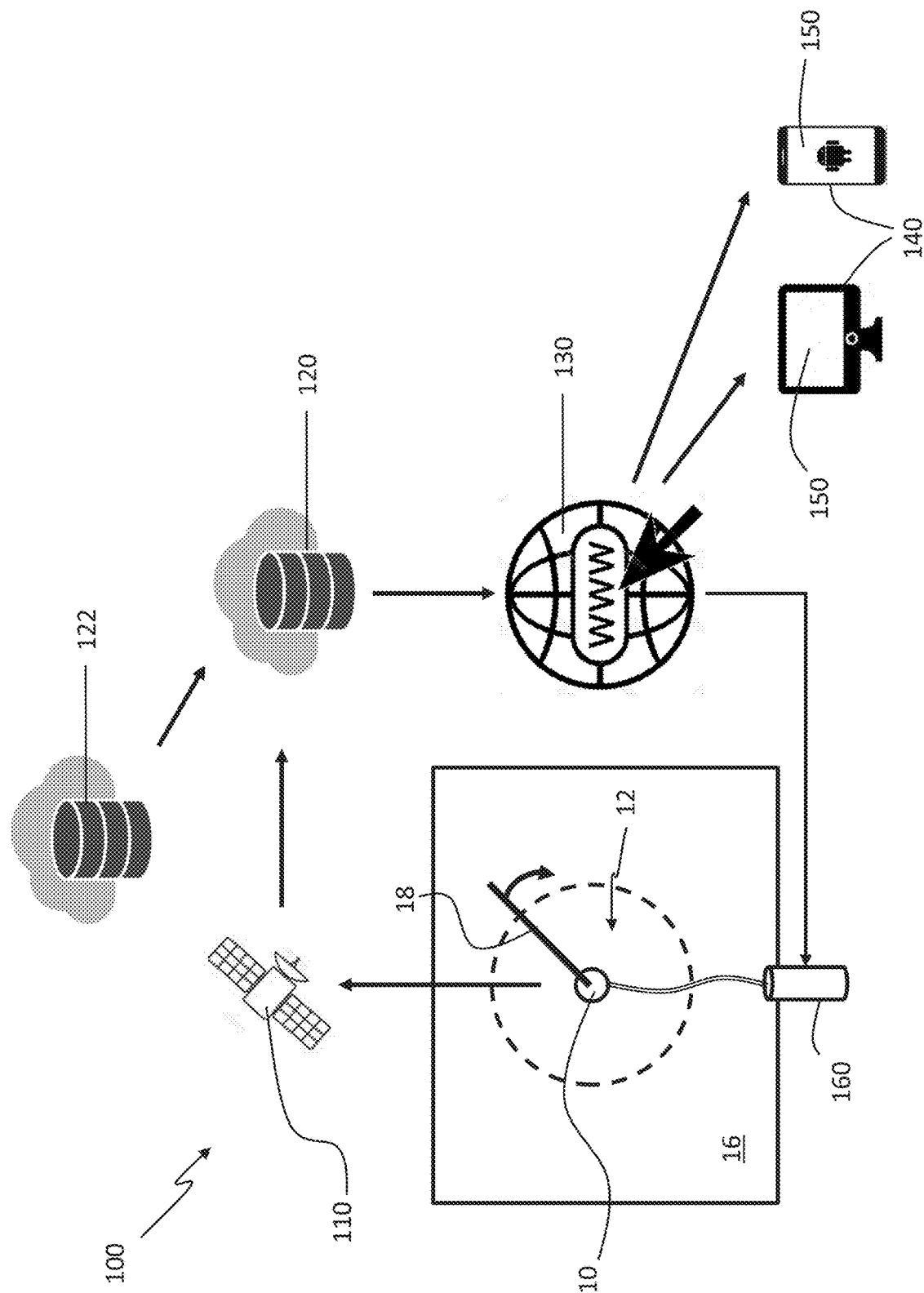
FIG. 9 is a diagrammatic illustration of a system for cosmogenic neutron sensing to detect moisture, in accordance with the first exemplary embodiment of the present disclosure.

FIG. 9 is a diagrammatic illustration of a system for cosmogenic neutron sensing to detect moisture 100, in accordance with the first exemplary embodiment of the present disclosure. As shown, the system for cosmogenic neutron sensing to detect moisture 100, which may be referred to herein simply as the 'system 100' includes the apparatus 10 for cosmogenic neutron sensing to detect moisture, as described in FIGS. 1-8C. The apparatus 10 may be placed within an agricultural field 16 or region, e.g., crop field with trees, plants, or other vegetation, and be either movable or immovable within the field 16. The apparatus 10 has a footprint for which it is capable of detecting moisture which is identified by the measurement surface 12 encircled in broken lines.

In operation, the apparatus 10 measures various physical properties such as fast neutron flux, pressure, temperature and humidity. The data collected is uploaded from the apparatus 10 to a network-enabled device 110, such as a satellite, cellular telemetry, Wi-Fi, general radio transmitter, or another communication medium. Data can be uploaded from the apparatus 10 and also downloaded by the apparatus 10 from the network-enabled device 110. The data may then be transmitted to central control center or central server 120 which can be a computerized, physical server, cloud server or website communicates back-and-forth to each apparatus 10. Some calibration data relevant to soil moisture calculations is available on the Internet 130, generally, and the system 100 can collect this data at the central server 120 such that it can be used to calculate properly calibrated soil moisture based upon raw data uploaded from the apparatus 10. In one of many alternatives, it can download calibration data to the apparatus 10 where calibration calculations can be done locally.

When a plurality or cluster of apparatuses 10 are used together, a single apparatus 10 may be capable of collecting some of the data (temperature, humidity, pressure) which can be used to calculate or calibrate soil moisture for multiple apparatus 10, or even multiple systems 100. This ability to rely on one apparatus 10 or system 100 to feed data to other apparatuses 10 or other systems 100 may reduce the overall cost of sensor hardware and communications. Additionally, data may be received from external sources 122, such as other databases or other systems. The system 100 may be accessible by a user through a computing device 140 having a display interface 150, such as a desktop, mobile phone, or other computing device which connects to the system 100 through the Internet 130 or another network connection. Additionally, these connections may be used by the user to access the system 100, review and analyze the data, and otherwise utilize the system 100. Additional functionality of the system 100 and data output capabilities are described in further detail relative to FIGS. 16-17.

Figure 10:
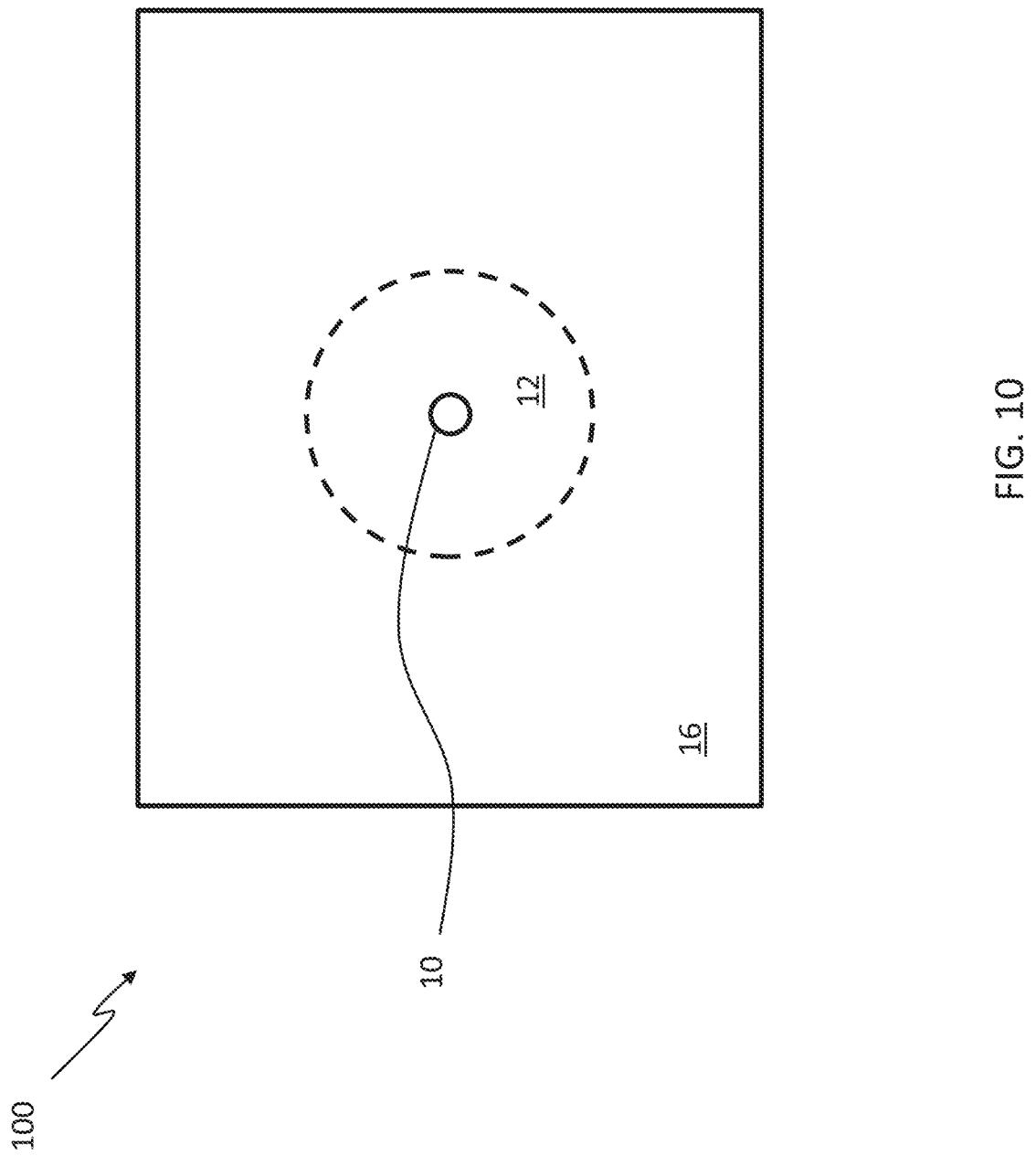
FIGS. 10-11 are diagrammatic illustrations of the system for cosmogenic neutron sensing to detect moisture of FIG. 9, in accordance with the first exemplary embodiment of the present disclosure.
Figure 11:
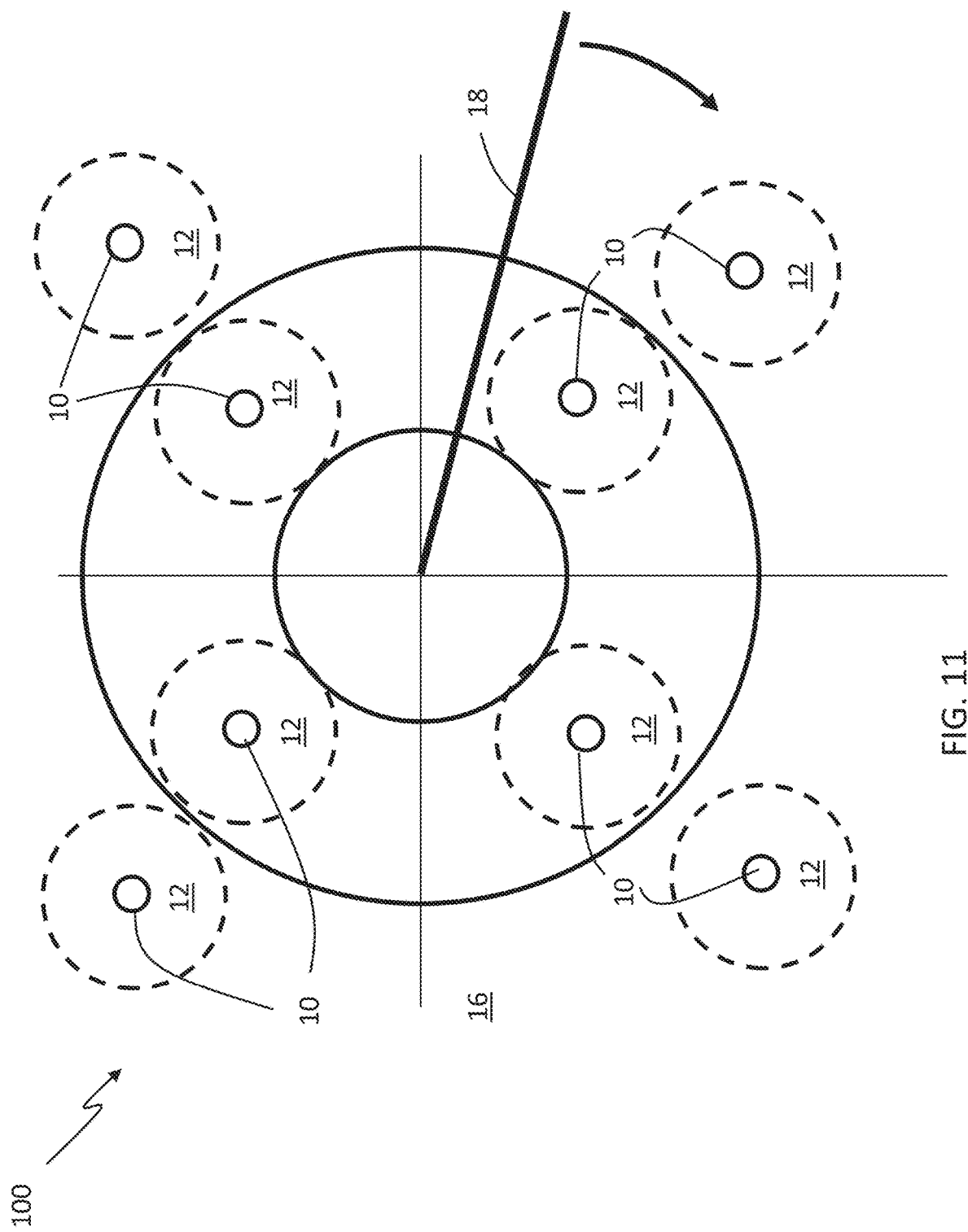

FIGS. 10-11 are diagrammatic illustrations of the system for cosmogenic neutron sensing to detect moisture 100 of FIG. 9, in accordance with the first exemplary embodiment of the present disclosure. In particular, FIG. 10 illustrates the use of the apparatus 10 in a stationary position, while FIG. 11 illustrates the use of a plurality of apparatuses 10 in stationary positions within an agricultural field. In FIG. 10, a single apparatus 10 is deployed in an agricultural field 16 that is irrigated by rain, sprinklers, drip irrigation, or another non-moving irrigation system. The apparatus 10 measures average soil moisture over a large fraction of the field 16, in particular, within a measurement surface 12 which overlaps a portion of the field 16. In FIG. 11, multiple apparatuses 10 are positioned within a field 16 which may be irrigated by a moving irrigation platform, such as a rotating center pivot irrigator 18. The apparatus 10 may be positioned in fixed locations around the field 16 in predetermined positions to ensure the desired sensing coverage is achieved. As the rotating center pivot irrigator 18 rotates around the field, it irrigates the field 16 along the portions which correspond to measurement surfaces 12 of the apparatuses 10, respectively, and portions in between those measurement surfaces 12. The apparatuses 10 are able to provide delayed or real-time soil moisture monitoring of the field 16, including a map of the field, that will broadly measure the changing soil moisture caused by the rotating center pivot irrigator 18. The apparatuses 10 placed in each region of the field 16, in this mode, continually monitor the region where they are deployed to produce soil moisture data which can be interpolated for the entirety of the field 16.

Figure 12:
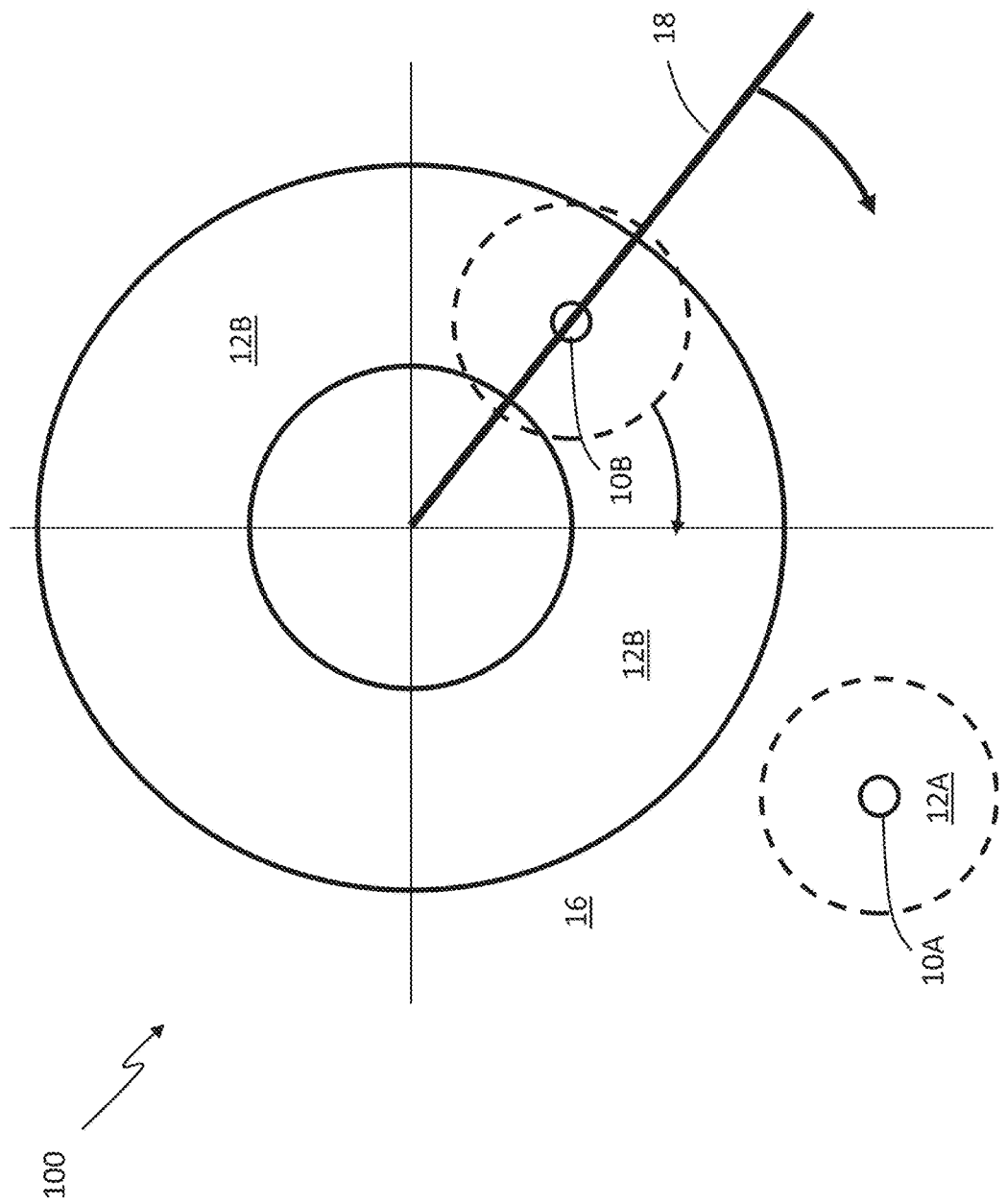

It is also possible to use a combination of stationary apparatuses 10 and mobile apparatuses 10, which are depicted in FIGS. 12-13, which are diagrammatic illustrations of the system for cosmogenic neutron sensing to detect moisture 100 of FIG. 9, in accordance with the first exemplary embodiment of the present disclosure. As shown in FIG. 12, a field 16 is irrigated by a rotating center pivot irrigator 18, which rotates around the field 16 in 360°. One apparatus 10A is placed within the field in a stationary position, such that the apparatus 10A has a stationary measurement surface 12A on the field 16. An additional apparatus 10B is mounted to the frame of the rotating center pivot irrigator 18, such that it is carried on the rotating center pivot irrigator 18 as it moves around the field 16. The measurement surface 12B of the mobile apparatus 10B is ring-shaped, since it traces out an annulus of measurement as the center pivot irrigator 18 rotates, i.e., since the apparatus 10B is moved in a circular path and has a lateral coverage area which extends outside of the direct footprint of the apparatus 10B itself. This allows a mapping of the moisture of the annular region to be made. At the same time, the apparatus 10A may provide a stationary reading of the moisture within its measurement surface 12A.

Due to the motion of the apparatus 10B, the PV panel may be pointed straight upward and receives sunlight at a glancing angle. This reduces the PV panel efficiency but avoids the complexity of having to change the angle of the PV panel with respect to sun as the center pivot irrigator 18 moves. The low power operation of the apparatus 10 is helpful since PV panel power production is not normally optimal. Data from the apparatuses 10A, 10B can be uploaded to the system 100 on any cadence. It may be preferred for uploads to occur at periodic intervals such as, for example, hourly, every few hours, or daily. Data is subject to Poisson counting statistics which means that 3 to 6 hour averaging windows may be appropriate. This averaging time frame may be timed to be consistent with the motion of the pivot arm.

FIG. 13 illustrates a similar example, but instead of a center pivot irrigator 18, the irrigator is a linear motion irrigator 19 which moves in a linear motion across the field 16. As the linear motion irrigator 19 moves, an apparatus 10B which is carried on the arm of the linear motion irrigator 19 detects moisture along a measurement surface 12B having a linear path. One or more stationary apparatus 10A may also be used to detect moisture in a stationary measurement surface 12A within the field 16.

Figure 14:
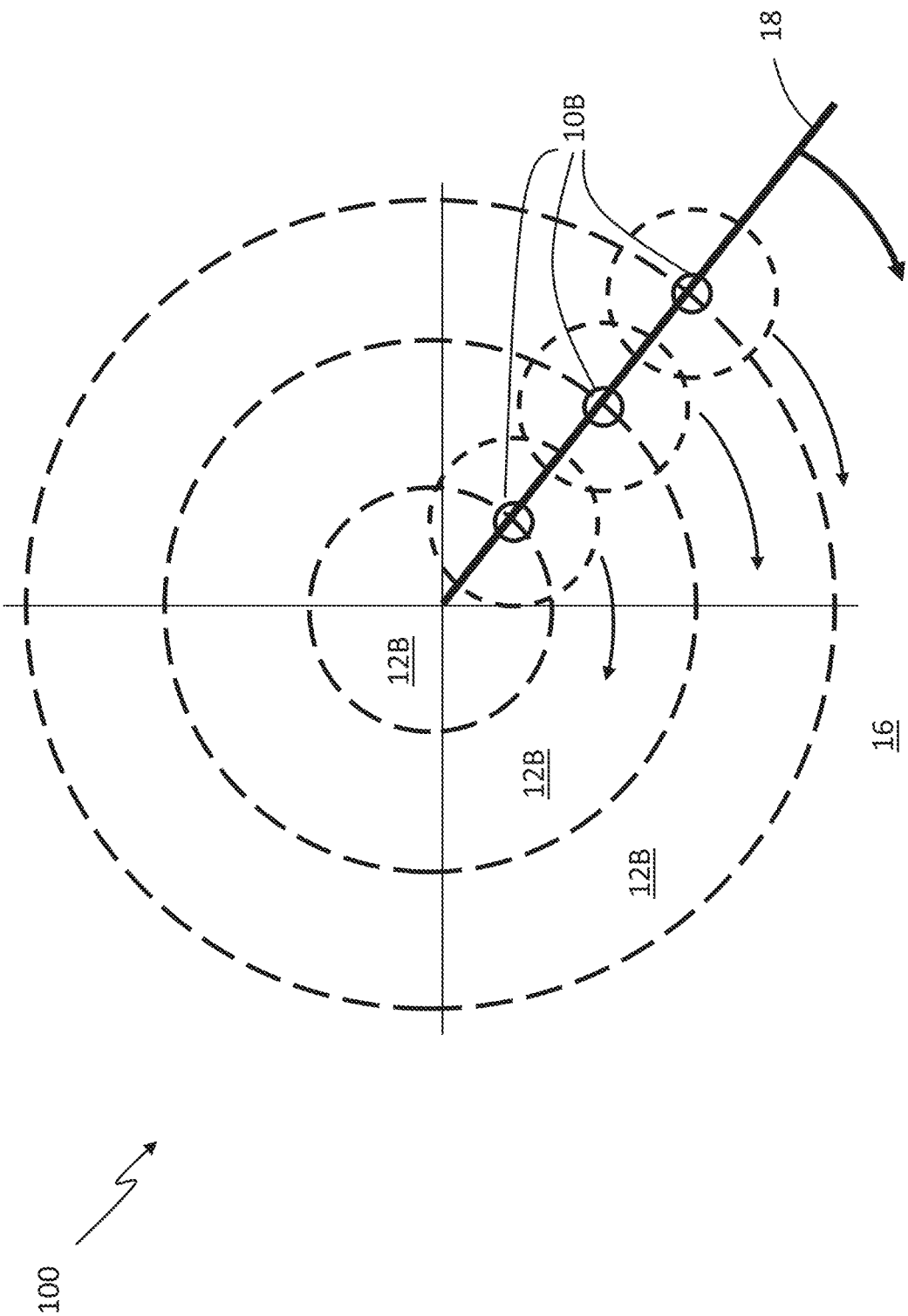
FIGS. 14-15 are diagrammatic illustrations of the system for cosmogenic neutron sensing to detect moisture of FIG. 9, in accordance with the first exemplary embodiment of the present disclosure.
Figure 15:
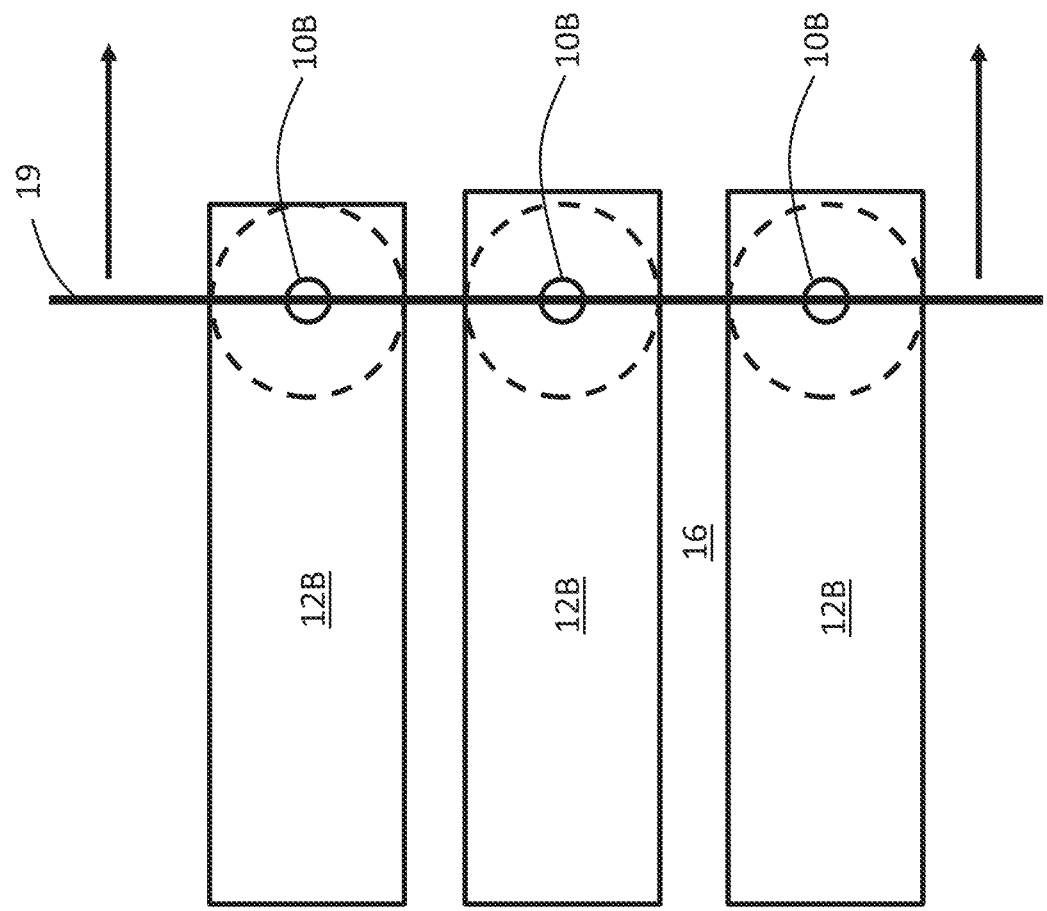

The use of mobile apparatuses 10 alone may also be beneficial to the system 100. To this end, FIGS. 14-15 are diagrammatic illustrations of the system for cosmogenic neutron sensing to detect moisture 100 of FIG. 9, in accordance with the first exemplary embodiment of the present disclosure. As shown in FIGS. 14-15, a plurality of apparatuses 10B are mounted to the frame of either a rotating center pivot irrigator 18, as shown in FIG. 14, or a linear motion irrigator 19, as shown in FIG. 15. As the rotating center pivot irrigator 18 or the linear motion irrigator 19 move, the apparatus 10B are moved around or across the field 16 to generate measurement surfaces 12B which correspond to the motion of the apparatus 10B. For instance, in FIG. 14, the measurement surfaces 12B of the three apparatuses 10B illustrated are shaped as a circle which substantially correlates to the footprint of the rotating center pivot irrigator 18. In FIG. 15, the measurement surfaces 12B are individual rectangles which each correspond to the linear movement of the apparatus 10B.

In FIG. 14, the set of apparatuses 10B are used and installed on a center pivot to cover a large fraction of the field 16 and create a moisture map of the field 16 as the pivot rotates over some time period. After a reliable map has been created, it may be possible to remove some of these apparatuses 10B and leave only a single apparatus 10B. The single apparatus 10B that is left in place may be used to measure within its own footprint and to infer the relative values in measurement regions corresponding to the sensors that have been removed. A similar approach may also be used with linear motion irrigators 19, as shown in FIG. 15, where after a reliable map has been created by the apparatuses 10B, all but one may be removed. The single apparatus 10B that is left in place may be used to measure within its own footprint and to infer the relative values in measurement regions corresponding to the sensors that have been removed.

While FIGS. 10-15 provide examples of the placement and movement of the apparatuses 10 within the system 100, it is noted that other arrangements are possible, including mounting the apparatuses 10 on other irrigation structures (vehicles, drones, poles, etc.) or positioning the apparatuses 10 in such a way to generate the desired coverage with minimal apparatus 10 usage.

Figure 16:
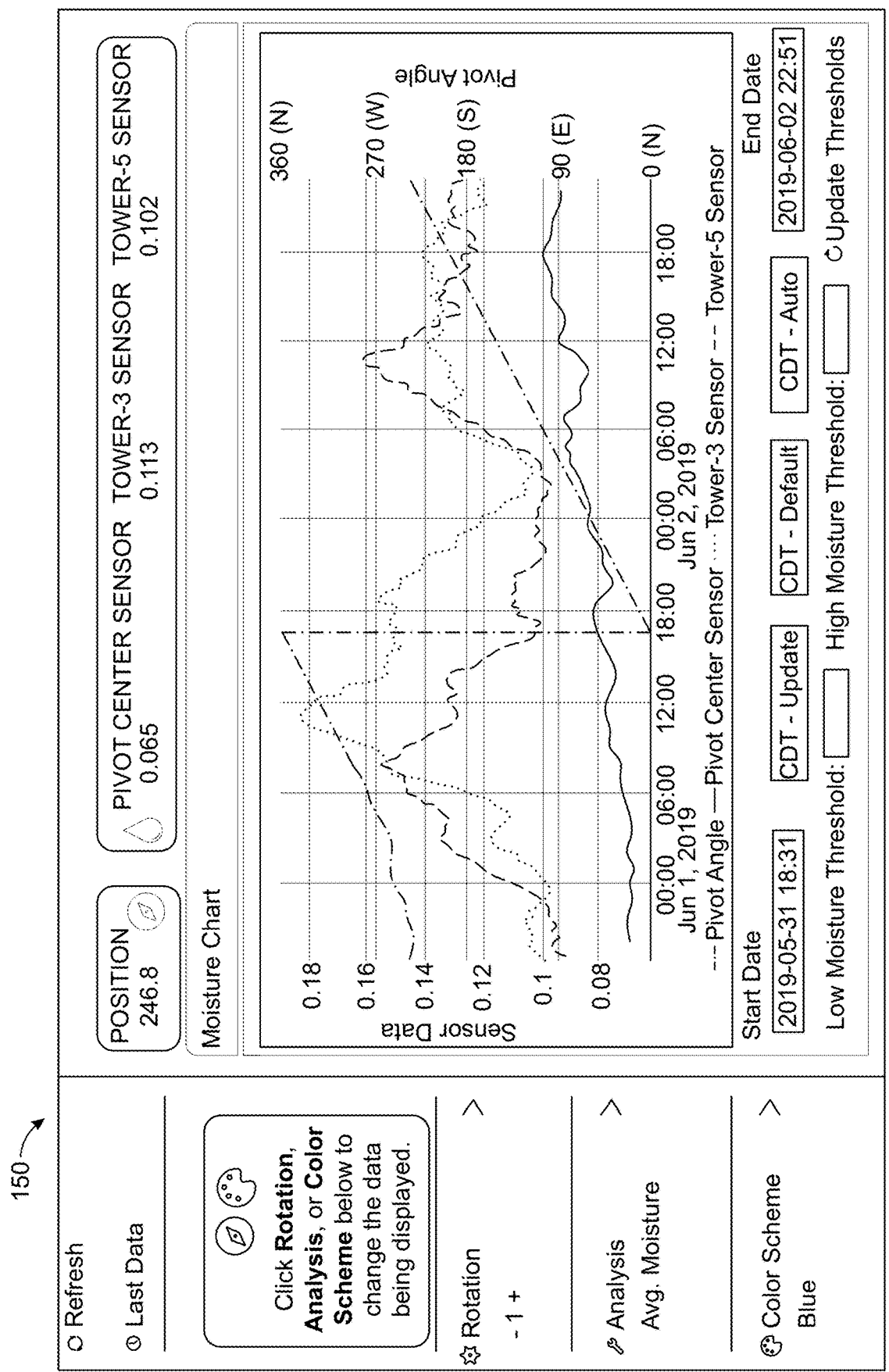
FIGS. 16-17 are illustrations of the display interface 150 of the system for cosmogenic neutron sensing to detect moisture of FIG. 9, in accordance with the first exemplary embodiment of the present disclosure.
Figure 17:
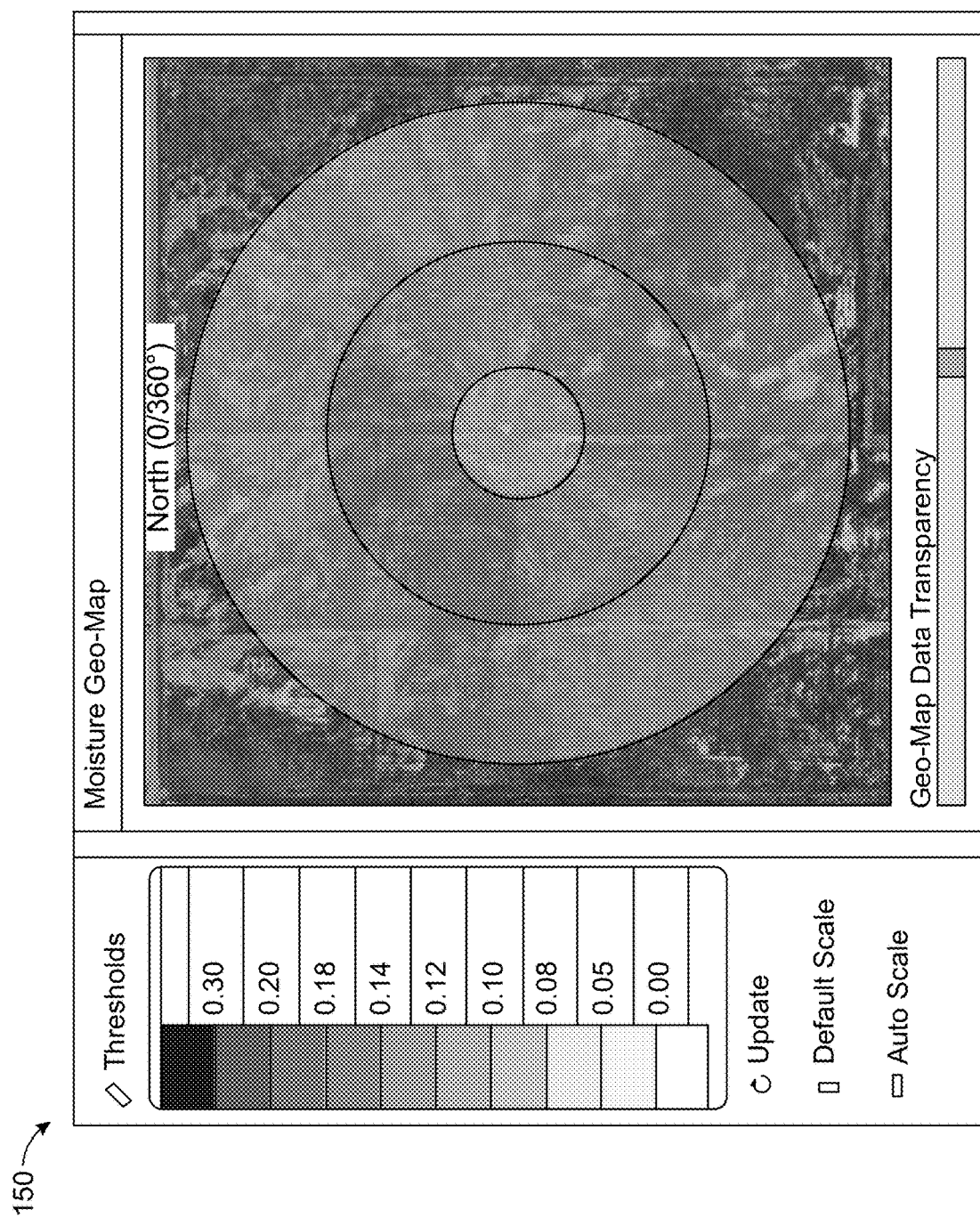

The data collected by the apparatus 10 or apparatuses 10 of the system 100 can be used in various ways, but a primary use may be to display the relevant data to a user through a display device, such as a display interface 150 of the computing device 140, as discussed relative to FIG. 9. FIGS. 16-17 are illustrations of the display interface 150 of the system for cosmogenic neutron sensing to detect moisture 100 of FIG. 9, in accordance with the first exemplary embodiment of the present disclosure. With reference to FIGS. 9 and 16-17, the central server 120 can host a website for an end user to access soil moisture data on the display interface 150, or it can send data to a website hosted elsewhere. A webpage for each apparatus 10 or cluster of apparatuses 10 may be viewed by the end user with a PC, tablet or smart phone.

Numerical or graphical data displayed may depend upon the type of apparatus 10 installation. A stationary apparatus 10 may show a strip chart of soil moisture over time, as shown in FIG. 16. Deployment of an array of stationary apparatuses 10 throughout an irrigated field can produce a continuous soil moisture map of the field at all times. This map shows the variation in soil moisture as a function of position in the field at all times. The spatial resolution of the map depends upon the number and placement of the apparatuses 10. This technique can be used to measure variation in soil moisture across fields that are irrigated by rain, flooding, drip systems, fixed sprinklers, and mobile irrigation devices such as linear and center pivot irrigators.

A moving apparatus 10 in a vehicle or, on a moving irrigation platform, for example, may include a 2D graph of soil moisture that varies over time, as shown in FIG. 17. Instead of installing an array of stationary apparatuses 10 throughout a field to generate a soil moisture map, one can move one or more apparatuses 10 through the field on a mobile platform. Soil moisture is measured at different locations over time and a map is produced. The spatial resolution of the map will depend upon the number of sensors used in the mobile system and the speed at which the mobile system moves. Such a map can be produced by one or more apparatuses 10 moving throughout the field by any means including on a vehicle (manually or autonomously operated) or carried by a person or animal. Additionally, the apparatuses 10 could be transported throughout the field by a moving irrigation platform such as a linear or center pivot irrigator. In this case, the apparatuses 10 could be attached directly to the moving irrigation platform, or the apparatuses 10 could be connected to a mobile system such as a trailer which is pushed or pulled through the field by the motion of the moving irrigation platform. In the special case of a quarter section center pivot irrigation system, there are typically 8 to 9 towers with wheels that support the structure and provide locomotion. The spacing between these towers is a good match for the radial sensitivity function or 'footprint' of the standard apparatus 10. Placing apparatuses 10 on towers 3, 5 and 7, for example, covers a significant portion of the field within the sensor footprint and allows for soil moisture maps with good spatial resolution to be produced.

For either stationary or mobile apparatuses 10, the system 100 soil moisture data can be interpreted by an end user, or it can be used to automatically control an irrigation system based upon an irrigation prescription. For example, the system 100 can connect directly, at the hardware level, to an electronic controller to automatically control an irrigation system 160, as depicted in FIG. 9, such that the application of water to the field, such as with a center pivot irrigator 18, can be correlated to the detected areas of that field which require more water, whereas areas of the field which have sufficient soil moisture may skip irrigation sessions. Alternately, the central server 130 connected to the apparatus 10 may interface via a software API with an irrigation control system that has a web interface. It is also possible for the central server 130 to contain soil moisture data and diagnostic data relevant to the functioning of the apparatus 10, where automatic alerts are issued by the central server 130 based upon diagnostic data.

A soil moisture map can be used to generate an irrigation prescription that is intended to make the soil moisture match the user's intention. Generally, in agriculture, the goal is to make the soil moisture homogeneous across the field and to control its average value, to keep it within an acceptable range. Often flood irrigated fields can be flooded in sections that are separately controlled. To control soil moisture variation on size scales consistent with these sections, the timing of flooding and the amount of water used within each section can be adjusted based upon the soil moisture map. For fields with fixed sprinklers, the timing and amount of water applied to the field can be adjusted to create an optimal field average value of soil moisture. For fields with fixed sprinklers with variable control, the timing and amount of water applied by each sprinkler head can be individually adjusted according to the soil moisture map to create the ideal result which is commonly uniform soil moisture within some acceptable range of values.

In the case of mobile irrigation platforms such as linear or center pivot irrigators, there are a few ways to adjust irrigation in response to a soil moisture map. First, the timing and average amount of water deposited by the irrigation system can be selected to achieve a desired field average soil moisture value. Additionally, some moving irrigation systems allow variable control of watering along their length. In the case of a center pivot, this capability can be used to control the amount of water deposited as a function of radius from the center. This can be used to adjust for radial variations in a soil moisture map. The speed of rotation of a center pivot can also be adjusted. This capability is useful in adjusting the amount of water that is deposited as a function of the angle of the pivot. For example, if one quadrant of a quarter section is wetter relative to another section, then the pivot can be made to rotate faster through the wetter section to deposit less water and to rotate slower through the dryer section to deposit more water, thus achieving a more homogenous deposition of water as a function of pivot angle.

Figure 18:
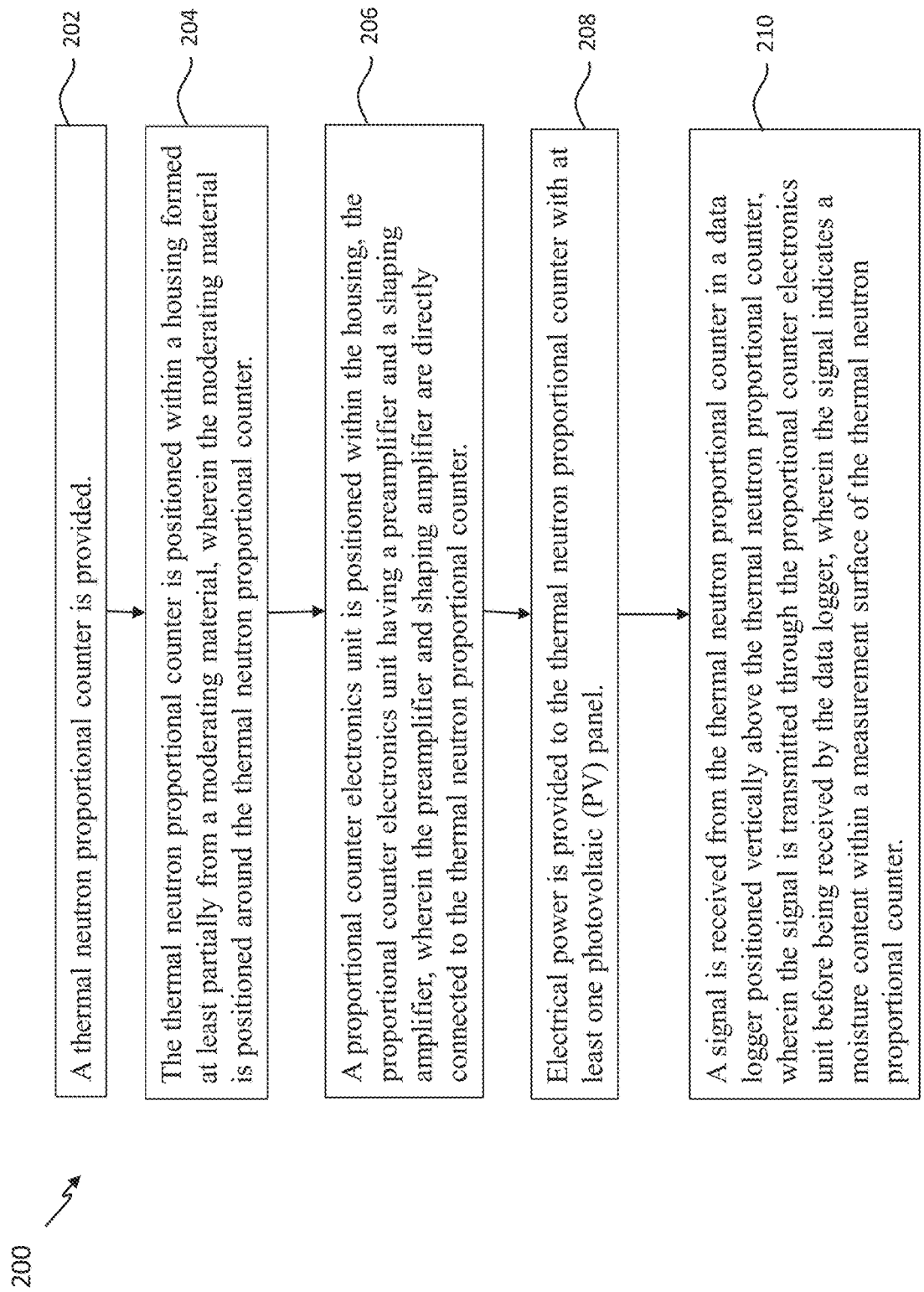
FIG. 18 is a flowchart illustrating a method of manufacturing an apparatus for cosmogenic neutron sensing to detect moisture in accordance with the first exemplary embodiment of the disclosure.

FIG. 18 is a flowchart 200 illustrating a method of manufacturing an apparatus for cosmogenic neutron sensing to detect moisture in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, a thermal neutron proportional counter is provided. The thermal neutron proportional counter is positioned within a housing formed at least partially from a moderating material, wherein the moderating material is positioned around the thermal neutron proportional counter (block 204). A proportional counter electronics unit is positioned within the housing, the proportional counter electronics unit having a preamplifier and a shaping amplifier, wherein the preamplifier and shaping amplifier are directly connected to the thermal neutron proportional counter (block 206). Electrical power is provided to the thermal neutron proportional counter with at least one photovoltaic (PV) panel (block 208). A signal is received from the thermal neutron proportional counter in a data logger positioned vertically above the thermal neutron proportional counter, wherein the signal is transmitted through the proportional counter electronics unit before being received by the data logger, wherein the signal indicates a moisture content within a measurement surface of the thermal neutron proportional counter (block 210). Any number of additional steps, functions, processes, or variants thereof may be included in the method, including any disclosed relative to any other figure of this disclosure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. An apparatus for cosmogenic neutron sensing to detect a moisture, the apparatus comprising:
   a thermal neutron proportional counter;
   a housing comprising at least partially a moderating material, wherein the housing is positioned around the thermal neutron proportional counter;
   a proportional counter electronics unit within the housing and having a preamplifier and a shaping amplifier, wherein the preamplifier and the shaping amplifier are directly connected to the thermal neutron proportional counter;
   at least one photovoltaic (PV) panel providing an electrical power to the thermal neutron proportional counter; and
   a data logger positioned vertically above the thermal neutron proportional counter and the proportional counter electronics unit, wherein a signal emitted by the thermal neutron proportional counter through the proportional counter electronics unit is received by the data logger, and wherein the signal indicates a moisture content within a measurement surface of the thermal neutron proportional counter.

2. The apparatus of claim 1, wherein the thermal neutron proportional counter further comprises at least one of:
   a helium-3 thermal neutron proportional counter;
   a boron trifluoride (BF3) thermal neutron proportional counter;
   a boron-lined (B10) thermal neutron proportional counter; or
   a lithium-6 metal foil thermal neutron proportional counter.

3. The apparatus of claim 1, wherein the at least one PV panel further comprises a plurality of PV panels, wherein at least one of the plurality of PV panels is positioned on each elongated side of the housing.

4. The apparatus of claim 1, further comprising a PV panel mounting structure connected to the housing, wherein the PV panel mounting structure has a movable arm to orientate the PV panel in a desired azimuthal angle.

5. The apparatus of claim 1, further comprising a vibration-reducing material interfaced at least partially between the thermal neutron proportional counter and an interior sidewall of the housing.

6. The apparatus of claim 1, further comprising at least one battery, wherein the data logger further comprises:
   an antenna;
   a wired or wireless communication interface; and
   a solar charge controller for controlling a charge of the at least one battery.

7. The apparatus of claim 1, wherein the moderating material further comprises HDPE, wherein the housing comprises, at least partially, HDPE sheets having edges thereof welded together.

8. The apparatus of claim 1, further comprising a lid removable from the housing, wherein the lid further comprises:
   a breather valve formed at least partially through the lid; and
   a sensor positioned proximate to the breather valve, wherein the sensor senses an environmental condition interior or exterior of the housing.

9. The apparatus of claim 1, further comprising an agricultural irrigation device, wherein the housing is mounted on the agricultural irrigation device.

10. A system for cosmogenic neutron sensing to detect a moisture in an agricultural location, the system comprising:
    a non-contacting, field-scale cosmogenic neutron sensor for measuring a soil moisture in a measurement surface, the non-contacting, field-scale cosmogenic neutron sensor having:
        a thermal neutron proportional counter,
        a housing comprising at least partially a moderating material, wherein the housing is positioned around the thermal neutron proportional counter;
        a proportional counter electronics unit within the housing and having a preamplifier and a shaping amplifier, wherein the preamplifier and the shaping amplifier are directly connected to the thermal neutron proportional counter;
        at least one power source providing an electrical power to the thermal neutron proportional counter; and
        a data logger positioned vertically above the thermal neutron proportional counter and the proportional counter electronics unit, wherein a signal emitted by the thermal neutron proportional counter through the proportional counter electronics unit is received by the data logger, and wherein the signal indicates a moisture content within a measurement surface of the thermal neutron proportional counter; and
    an agricultural irrigation device having at least one frame member, wherein the non-contacting, field-scale cosmogenic neutron sensor is mounted to the at least one frame member, and wherein the non-contacting, field-scale cosmogenic neutron sensor is positioned a spaced distance above a ground surface.

11. The system of claim 10, wherein at least a portion of the agricultural irrigation device is movable along a path, whereby a movement of the at least the portion of the agricultural irrigation device moves the non-contacting, field-scale cosmogenic neutron sensor along the path.

12. The system of claim 10, wherein the thermal neutron proportional counter further comprises at least one of:
    a helium-3 thermal neutron proportional counter;
    a boron trifluoride (BF3) thermal neutron proportional counter;
    a boron-lined (B10) thermal neutron proportional counter; or
    a lithium-6 metal foil thermal neutron counter.

13. The system of claim 10, wherein the at least one power source further comprises at least one photovoltaic (PV) panel positioned on one or more elongated sides of the housing.

14. The system of claim 13, further comprising a photovoltaic (PV) panel mounting structure connected to the housing, wherein the PV panel mounting structure has a movable arm to orientate the at least one PV panel in a desired azimuthal angle.

15. The system of claim 10, further comprising a vibration-reducing material interfaced at least partially between the thermal neutron proportional counter and an interior sidewall of the housing.

16. The system of claim 10, wherein the at least one power source further comprises at least one battery, and wherein the data logger further comprises:
    an antenna;
    a wired or wireless communication interface; and
    a solar charge controller for controlling a charge of the at least one battery.

17. The system of claim 10, wherein the moderating material further comprises HDPE, wherein the housing comprises, at least partially, HDPE sheets having edges thereof welded together.

18. The system of claim 10, further comprising a lid removable from the housing, wherein the lid further comprises:
    a breather valve formed at least partially through the lid; and
    a sensor positioned proximate to the breather valve, wherein the sensor senses an environmental condition interior or exterior of the housing.

19. A method of manufacturing an apparatus for cosmogenic neutron sensing to detect a moisture:
    providing a thermal neutron proportional counter;
    positioning the thermal neutron proportional counter within a housing formed at least partially from a moderating material, wherein the housing is positioned around the thermal neutron proportional counter;
    positioning a proportional counter electronics unit within the housing, the proportional counter electronics unit having a preamplifier and a shaping amplifier, wherein the preamplifier and the shaping amplifier are directly connected to the thermal neutron proportional counter;

providing an electrical power to the thermal neutron proportional counter with at least one photovoltaic (PV) panel; and receiving a signal from the thermal neutron proportional counter in a data logger positioned vertically above the thermal neutron proportional counter, wherein the signal is transmitted through the proportional counter electronics unit before being received by the data logger, and wherein the signal indicates a moisture content within a measurement surface of the thermal neutron proportional counter.

20. The method of claim 19, further comprising providing at least one bracket positioned on an exterior of the housing, wherein the at least one bracket is configured to allow the housing to mount to an agricultural irrigation device.

* * * * *